(12) United States Patent
Lin et al.

(10) Patent No.: US 7,902,255 B2
(45) Date of Patent: Mar. 8, 2011

(54) γ-BUTYROLACTONE COMPOUND AND PHARMACEUTICAL COMPOSITION THEREOF

(75) Inventors: Shinn-Zong Lin, Beitou Chiu (TW); Horng-Jyh Harn, Banchiau (TW)

(73) Assignee: Tzu Chi Buddhist General Hospital, Hualien (TW)

( * ) Notice: Subject to any disclaimer, the term of this patent is extended or adjusted under 35 U.S.C. 154(b) by 18 days.

(21) Appl. No.: 12/378,504

(22) Filed: Feb. 17, 2009

(65) Prior Publication Data

US 2010/0028461 A1    Feb. 4, 2010

Related U.S. Application Data

(63) Continuation of application No. 11/186,705, filed on Jul. 20, 2005, now abandoned, and a continuation-in-part of application No. 10/690,992, filed on Oct. 21, 2003, now Pat. No. 7,348,032.

(30) Foreign Application Priority Data

Jul. 16, 2003  (TW) .............................. 92119380 A

(51) Int. Cl.
*A61K 31/341*  (2006.01)
*A61K 31/343*  (2006.01)

(52) U.S. Cl. .......... 514/465; 514/473; 549/434; 549/475

(58) Field of Classification Search .................. 514/465, 514/473; 549/434, 475
See application file for complete search history.

(56) References Cited

OTHER PUBLICATIONS

Nishibe et al., Natural Medicines (Tokyo, Japan), 2002, vol. 56(1), p. 13-16 (abstract from STN search report).*

\* cited by examiner

*Primary Examiner* — Yong Chu
(74) *Attorney, Agent, or Firm* — Peter F. Corless; Dwight D. Kim; Edwards Angell Palmer & Dodge LLP

(57) ABSTRACT

A γ-butyrolactone compound as shown in Formula (I) and pharmaceutical composition thereof:

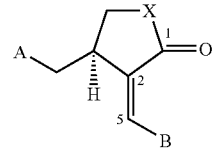

Formula (I)

wherein X=N, O, S, Se; and A and B are selected from substituents having the following formula:

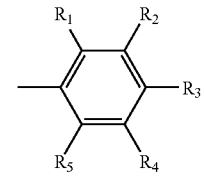

wherein $R_1$, $R_2$, $R_3$, $R_4$, and $R_5$ are selected from a hydrogen atom, a halogen atom, a hydroxyl group, a mercapto group, an amino group, an alkoxy group, and a nitro group. The γ-butyrolactone compound and pharmaceutical composition thereof butyrolactone have inhibitory effects on hepatoma, ovarian cancer, breast cancer, lung cancer, malignant glioblastoma or colorectal carcinoma, and are cytotoxic with high specificity to inhibit Paclitaxel-resistant tumor cells at later stage of chemotherapy without any damage on normal cells.

5 Claims, 24 Drawing Sheets

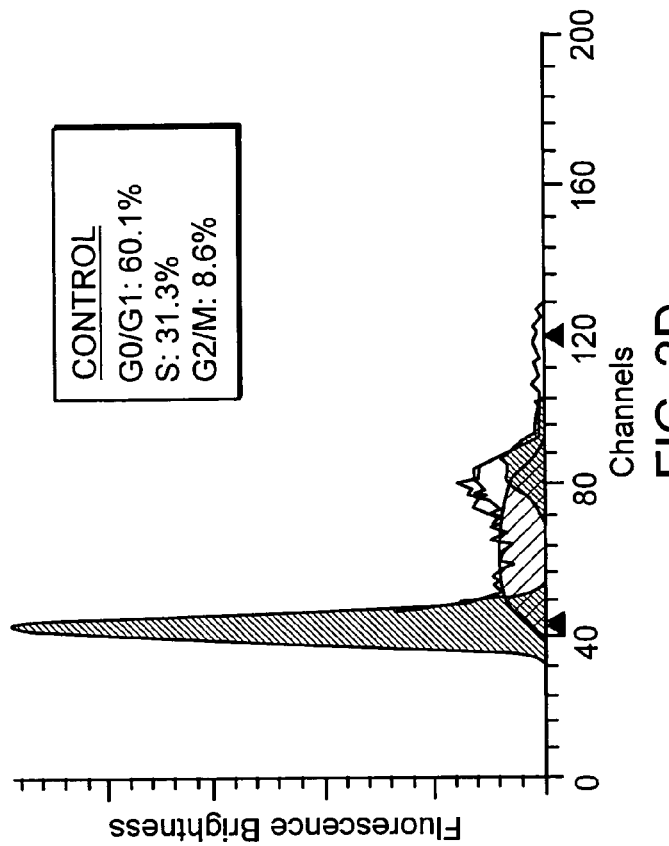
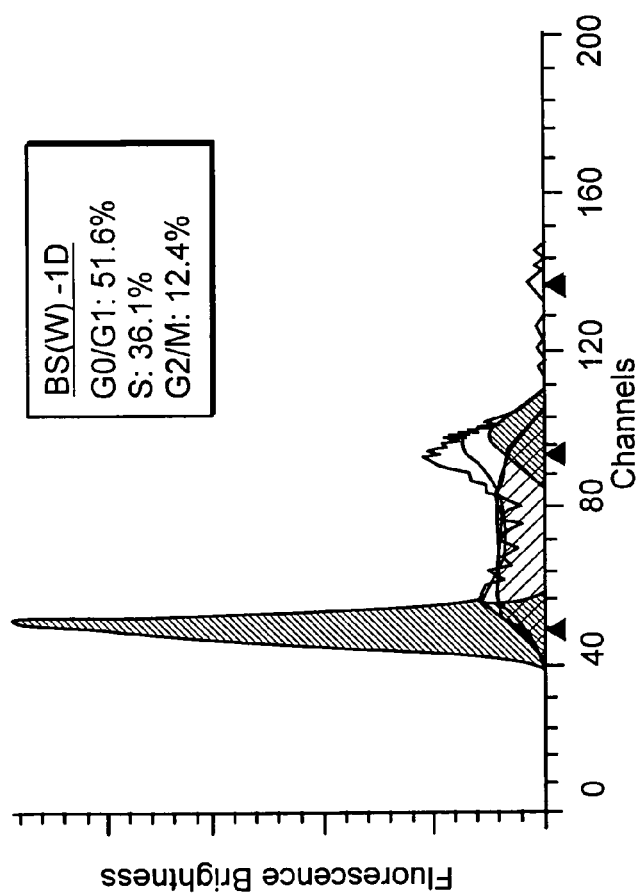

BS-AE (A549-T12)

BS-8 (A549-T12)

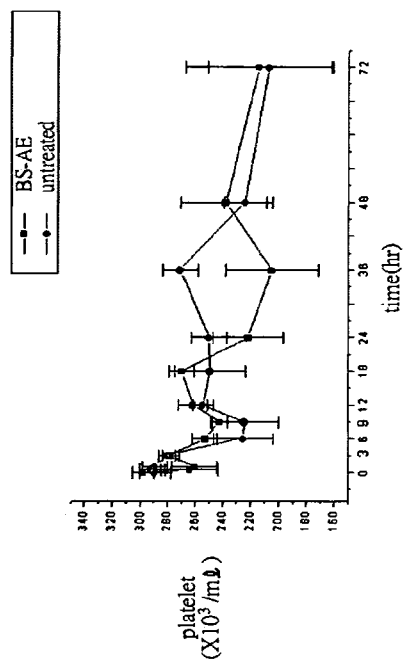
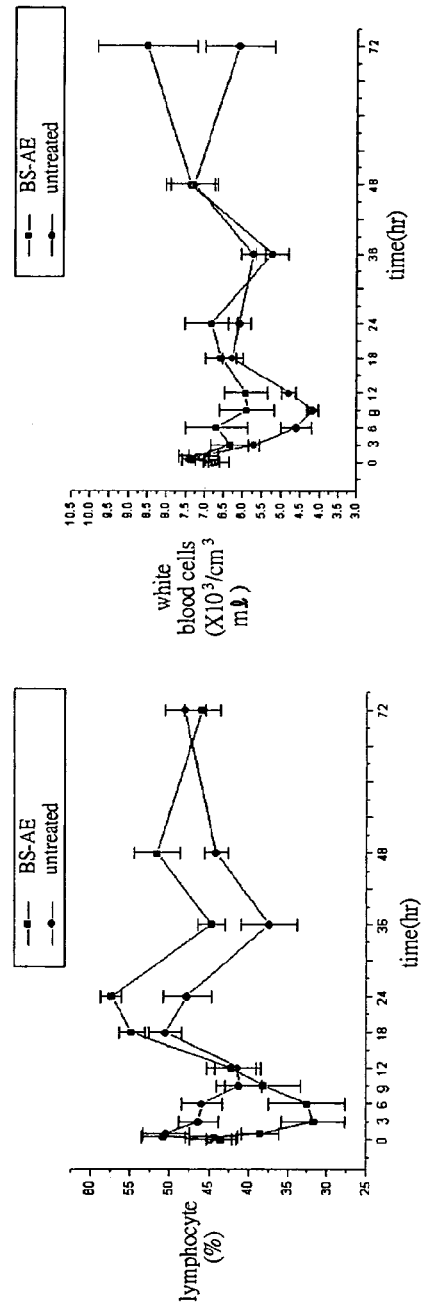
FIG. 15A
FIG. 15B
FIG. 15C

γ-BUTYROLACTONE COMPOUND AND PHARMACEUTICAL COMPOSITION THEREOF

The present application is a Continuation Application of U.S. Ser. No. 11/186,705, filed Jul. 20, 2005, which is a continuation in part of U.S. Ser. No. 10/690,992, filed Oct. 21, 2003, which in turn claimed the prior benefit of Taiwan application number 092119380, filed Jul. 16, 2003, each of which is incorporated herein by reference in its entirety.

FIELD OF THE INVENTION

The present invention relates to a novel compound and pharmaceutical composition thereof for treating mammalian cell proliferative disorders, chemo-therapy resistance and virus infections, particularly a novel γ-butyrolactone compound and pharmaceutical composition thereof for treating human malignant tumours such as hepatoma, lung cancer, ovarian cancer, breast cancer, human malignant glioblastoma, colorectal cancer, malignant brain spongiocyte lump and the like; chemo-therapy resistance such as paclitaxel and for treating RNA virus infections.

BACKGROUND OF THE INVENTION

Cancer, a cell proliferative disorder, is the leading cause of death worldwide. In 1993, Boring et al. estimated approximately 526,000 deaths from cancer alone in the U.S. each year. For example, breast cancer has been the leading cause of death from cancer in woman between the age of 40 and 55. And with increasing pollutions, the incidence of developing ovarian carcinoma, lung cancer, liver cancer and skin cancer has also increased. Studies from Fitzpatrick et al. in 1986 indicated the number of cancer occurrence has increased six times since 1945, revealing the urgent need for a novel method in diagnosis and treatment for cancer.

It was found from the current cancer studies that the senescence, replication and division of eukaryocyte are all regulated by the cell cycle. During a cell replication, chromosome numbers and deoxyribonucleic acid (DNA) content of the cell increased from 2N to 4N in order to produce two daughter cells after cell mitosis, so that each daughter cell has 2N chromosomes. In 1995, Blackburn et al. discovered a repeat sequence at the end of each chromosome, (5'TTAGGG), which is now known as a telomere is shortened after each mitotic cycle. And when the telomere shortens to a critical length, the telomere that covers the terminal end of the chromosome becomes sticky and causes abnormal pairing of the chromosomes and even a cell death in some cases.

In 1995, Feng et al. discovered a high expression of a ribonucleoprotein complex called telomerase that binds on the telomere at the end of the chromosome from the genetic studies of germ-line cells, stem cells, and tumour cells. The role of this telomerase is to maintain the telomere length, preventing the telomere to become shortened after multiple mitoses. The presence of telomerase helps the cell to escape from the cell cycle and become immortal.

Further research on telomerase activity using Telomerase Repeat Amplification Protocol (TRAP), lead to the finding of significant high telomerase activity in tumour cells and in germ cells, whereas almost no telomerase activity is found in normal somatic cells. In 1994 and 1995, Kim and Broccoli et al have also demonstrated an important role of telomerase in controlling apoptotic cascade of tumour cells. Thus, telomerase activity and its expression level are useful in cancer diagnosis and prognosis during cancer treatment due to its high specificity.

On the other hand, based on years of clinical experiences in Chinese medicine, 50 to 60 of Chinese herbs estimated to possess anti-tumour effect are selected using TRAP activity assay. Among these, *Panax ginseng, Glycyrrhiza uralensis, Bupleurum scorzonerifolium, Phellodendron amurense, Angelica sinensis, Gentiana scabra,* and *Scutellaria baicalensis* have proved to be very effective in the treatment of malignant tumours. Moreover, in comparison with current anti-cancer drugs, those Chinese herbs have shown less side effects, like reduction in number of white cells, cachexia and so on. Thus, extraction of anti-cancer components from Chinese herbs opens up a new source of novel anti-cancer drug screening.

Further, as an example, paclitaxel injection (commercially known as TAXOL), widely used as a potent chemotherapeutic agent to treat a variety of solid cancers, has a major component of Taxanol which is first isolated from the Pacific yew tree and represented by the following formula: (a molecular formula of $C_{47}H_{51}NO_{14}$, molecular weight of 854 Da and a diterpene core)

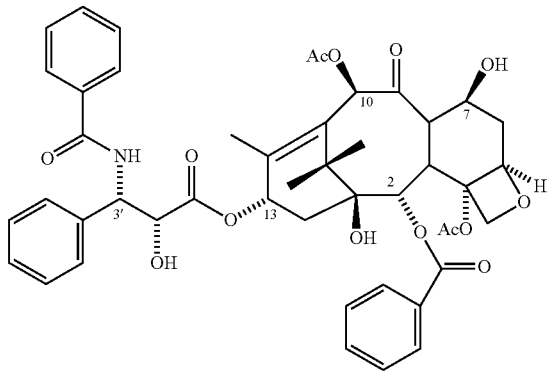

Paclitaxel injection is mainly used in treating ovarian cancer breast cancer metastasis, lung cancer and melanoma via its chemical mechanism of cytotoxicity on tumor cells by inhibiting depolymerization of microtubulin by combining to β-tubulin of cell cytoskeleton in the ratio of 1:1, so as to interrupt cell mitosis and initiate cell death for the tumour cell (Blafosklonny et al., 1995). Therefore, application of Taxane drugs, such as Taxol, is effective in delivering toxicity towards tumour cells at the initial stage of ovarian cancer, improving the survival rate of the patient by about 15% in two years.

However, as the treatment was prolonged, many tumour cells gradually developed drug resistant to Paclitaxel. From the recent research, it was discovered that some of Paclitaxel resistant cells exhibit different β-tubulin expression level and different electrophoresis mobility from the conventional tumour cells. Research works from Rao et al. in 1995 have shown that tumour cells (for example human lung tumour cell lines A549-AT12) are capable of changing their configuration of six β-tubulin subunits to prevent binding with paclitaxel. Instead, paclitaxel is discharged out of the cell through ion pumping, making the tumour cells drug-resistant to paclitaxel after a period of chemotherapy.

Also, other anti-cancer agents such as 5-fluorouracil, epothilone, cisdiammine dichloroplatinum (Cisplatin), procarbazine and cyclophosphamide when clinically used alone or in conjunction with paclitaxel cannot provide a satisfactory outcome in terms of killing the cancer cells developed with drug resistant to paclitaxel. Results from cell culture experiment also indicate that it is difficult to effectively inhibit proliferation of Paclitaxel-resistant tumour cells using current anti-cancer drugs. In order to achieve a higher efficacy, it is often necessary to increase the administering dosage. For example, in an animal experiment, a rat may be injected with 300 mg/kg of paclitaxel. However this would result in high degree of necrosis for the normal cells due to its strong cytotoxicity possessed by the drug.

Thus, in order to improve the cytotoxic effect towards tumour cells at latter stages of chemotherapy, it is imperative to find and isolate anti-cancer components from Chinese herbs that have previously shown promising result in the treatment of cancer to effectively suppress proliferation of Paclitaxel-resistant tumour cell lines.

SUMMARY OF THE INVENTION

One aspect of the present invention is to provide a γ-butyrolactone compound and pharmaceutical composition thereof for treating mammalian cell proliferation disorders (such as human tumours such as hepatoma, lung cancer, ovarian cancer, breast cancer, human malignant glioblastoma, colorectal cancer and the like).

Another aspect of the present invention is to provide the γ-butyrolactone compound and pharmaceutical composition thereof having inhibitory effect on the growth of Paclitaxel-resistance tumour cell line and are named as Chaihulactone, Isochaihulactone, and other chaihulactone derivatives.

A further aspect of the present invention is to provide the γ-butyrolactone compound and pharmaceutical composition thereof which are cytotoxic to Paclitaxel-resistance tumour cell line with high specificity without causing harmful effects to the liver and kidney functions.

In order to achieve the foregoing and other aspects, a γ-butyrolactone compound and pharmaceutical compositions thereof are proposed for treating cancer cells of lung cancer, ovarian cancer, breast cancer, hepatoma, malignant glioblastoma and colorectal carcinoma. The γ-butyrolactone compound and pharmaceutical composition thereof further comprise at least one compound having a Z configuration or E configuration for its carbon 2(5) location at the core, and named respectively as "Chaihulactone", "Isochaihulactone" and their derivatives.

The γ-butyrolactone compound and pharmaceutical composition thereof comprise a compound having γ-butyrolactone as a core and Z configuration or E configuration for its carbon 2(5) location as illustrated in formula (I).

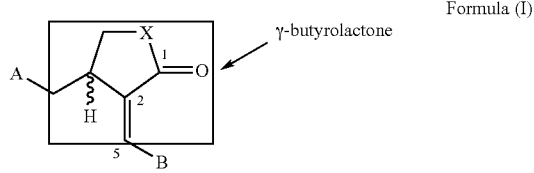

Formula (I)

wherein X=N, O, S, Se; and A and B can be selected from the following substituents:

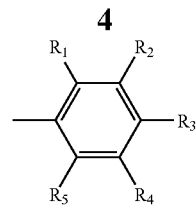

where $R_1$, $R_2$, $R_3$, $R_4$, and $R_5$ are selected from a hydrogen atom, a halogen atom, a hydroxyl group, a mercapto group, an amino group, an alkoxy group, and/or a nitro group In addition, Formula (I) further comprises novel heterocyclic compounds named chaihulactone, isochaihulactone and their derivatives as shown in Formula (II) and Formula (III). Chaihulactone, isochaihulactone and related analogues or derivatives of chaihulactone belong to a lignan skeleton. By comparing the formulae (I) (II) and (III), it is known that both chaihulactone and isochaihulactone are heterocyclic compounds each having γ-butyrolactone as a core and having a Z or E configuration at its carbon 2(5) location.

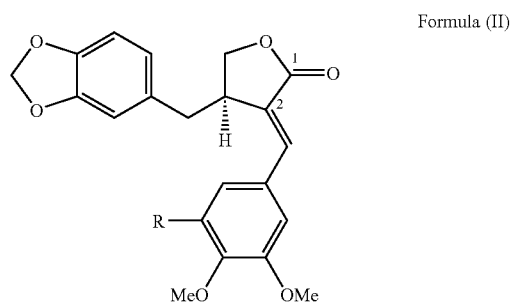

Formula (II)

wherein R represents an alkoxy group.

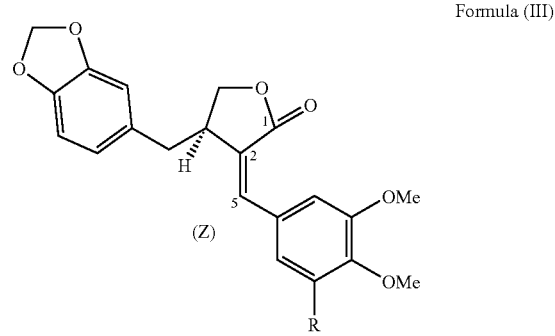

Formula (III)

wherein R represents a hydrogen atom, an alkoxy group, or an aromatic group.

From the experimental results of the preferred embodiment invention it is found that the γ-butyrolactone heterocyclic compounds and pharmaceutical composition thereof isolated from *Bupleurum scorzonerifolium* using different solvents (such as acetone or methanol) can all inhibit proliferation of tumor cells effectively. Different extracts extracted from *Bupleurum scorzonerifolium* using acetone are analyzed for their molecular structures to identify novel heterocyclic compounds such as chaihulactone, isochaihulactone and their derivatives.

From the experimental results of the preferred embodiments of the invention, it is found that as chaihulactone, isochaihulactone and their derivatives having γ-butyrolactone structure are added to cell lines of human lung cancer, hepatoma, malignant glioblastoma, and colorectal carcinoma, the telomerase activity of the treated tumor cells is significantly reduced by 5 times when compared to the untreated control group. A prominent cytotoxic effect was shown when the γ-butyrolactone heterocyclic compound and pharmaceutical composition thereof are added to the Paclitaxel-resistant tumor cell lines, indicating *Bupleurum scorzonerifolium* indeed contain active components for inhibiting tumor growth. The active components for inhibiting tumor growth refer to the novel compound and pharmaceutical composition thereof having a γ-core and having a Z or E configuration for its carbon 2(5) location at the core. Moreover, it is found that chaihulactone and isochaihulactone and their derivatives show the most prominent cytotoxic effects on tumors.

Furthermore, the inhibition of telomerase activity is observed in TRAP assay after the addition of γ-butyrolactone compound and pharmaceutical composition thereof. It is found that γ-butyrolactone compound and pharmaceutical composition thereof are capable of effectively inhibiting the telomerase activity and hTERT expression on human lung cancer cell lines A549, suggesting the potential of γ-butyrolactone compound to produce highly specific cytotoxicity to tumor cells.

In particular, after adding chaihulactone to Paclitaxel-resistant tumor cells such as A549-T12 cells (A549 cells resistant to Paclitaxel), it is found that the γ-butyrolactone compound and the pharmaceutical composition thereof are capable of inducing apoptosis of Paclitaxel-resistant tumor cells. From the results of flow cytometric analysis and Western blotting analysis to study the mechanism of *Bupleurum scorzonerifolium* extracts containing the γ-butyrolactone compound, it is found that *Bupleurum scorzonerifolium* extracts can induce high expression of tumor suppressors p21 and p53. As a result, the tumor cells are arrested at the spindle polymerisation stage (G2/M stage) of the cell cycle. Thus, in view of cell cycle regulation, the γ-butyrolactone compound and pharmaceutical composition thereof can serve as a microtubule stabilizing agent, having a mechanism similar to that of paxlitaxel, as both enhance microtubule polymerization. Accordingly, the tumor cells are arrested at G2/M stage and subsequently become junk cells leading to apoptosis.

BRIEF DESCRIPTION OF THE DRAWINGS

The present invention can be more fully understood by reading the following detailed description of the preferred embodiments, with reference made to the accompanying drawings, wherein:

FIG. 15A through 15C include a variety of statistical curves showing changes in platelets, white blood cells, and lymphocytes in the conscious mouse within 72 hours after intravenous administration of 400 mg/kg of BS-AE to the mouse.

DETAILED DESCRIPTION OF THE PREFERRED EMBODIMENTS

Figure 1:
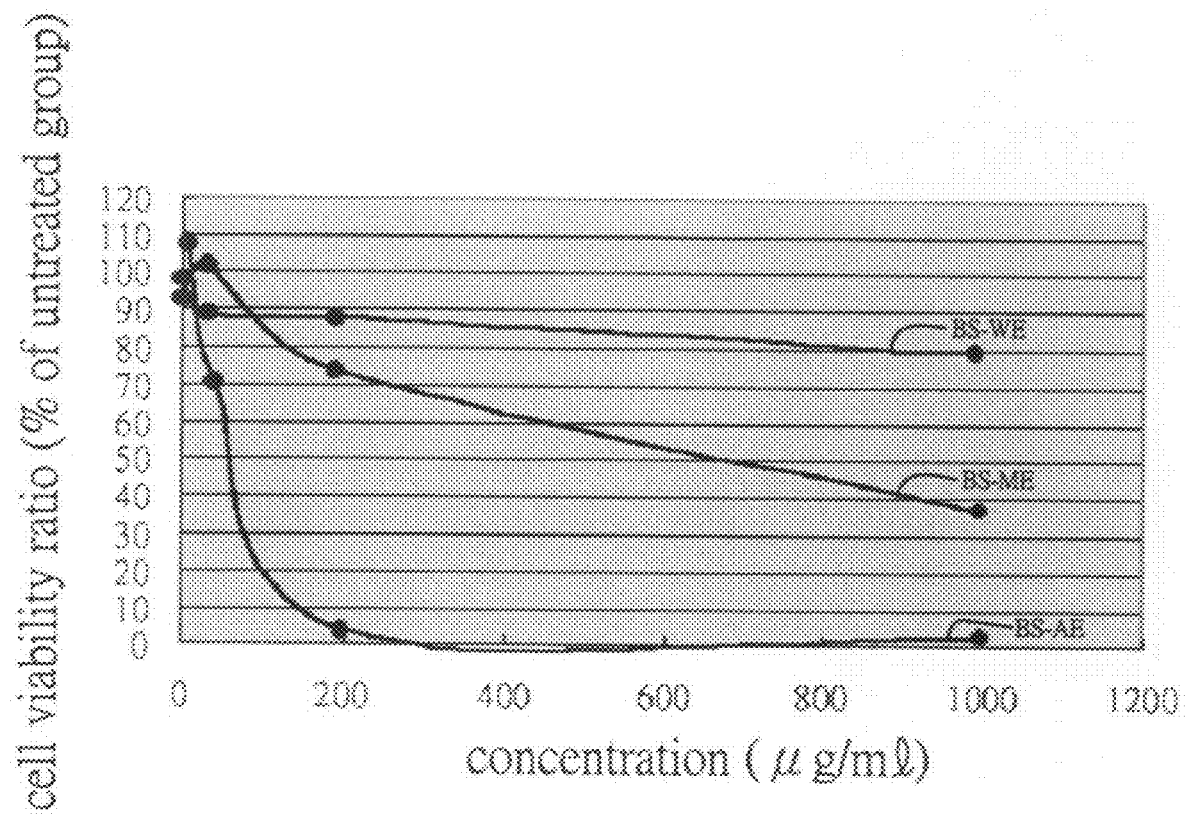
FIG. 1 is a schematic diagram showing change in cell viability ratio (in percentage of untreated group) for human lung cancer cell lines (A549 cells) subjected to a Methyl Thiazole Tetrazolium (MTT) assay with respect to the dosage (μg/ml) of *Bupleurum scorzonerifolium* extracts, such as Acetone Extract (BS-AE), Methanol Extract (BS-ME) and Water Extract (BS-WE) isolated according to the extracting method of the invention.

The present invention is described in detail in the following embodiments provided herein. It is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

This invention is comprised of at least 3 sections:

First of all, a method is described for manufacturing *Bupleurum scorzonerifolium* extract having inhibitory effects to human hepatoma cell line J5 and Hep G2, ovarian cancer cell line OVCAR-3, breast cancer cell line MCF 7, human malignant glioblastoma cell line DBTRG-05MD, lung cancer cell line A549 and WI-38, taxol resistant A549 subline A549-T12, and colorectal cancer cell line HT29 from crude *Bupleurum scorzonerifolium*.

Secondly, after the *Bupleurum scorzonerifolium* extract that is cytotoxic to the Txanol-ressitnace tumor cell line is obtained, a novel compound having tumor inhibitory effects is isolated from the *Bupleurum scorzonerifolium* extract. The novel compound and pharmaceutical composition thereof comprise at least one heterocyclic compound having γ-butyrolactone as a core and a Z-configuration or E-configuration for its carbon 2(5) location.

Thirdly, the novel γ-butyrolactone compound and pharmaceutical composition thereof are tested on the tumor cells lines in vivo and in vitro to examine the inhibitory effect of the γ-butyrolactone compound and pharmaceutical composition thereof on the tumor cell lines. Further, animal experiments are performed to evaluate the effects of the γ-butyrolactone compound and pharmaceutical composition thereof on the normal cells and tumor cells in a living organism, so as to evaluate the tumor inhibitory effects of the γ-butyrolactone compound and pharmaceutical composition thereof on hepatoma, ovarian cancer, breast cancer, lung cancer, malignant glioblastoma, or colorectal carcinoma.

In accordance with the method for manufacturing *Bupleurum scorzonerifolium* extract in the preferred embodiments of the invention, crude *Bupleurum scorzonerifolium* is ground into powder and submerged in acetone. After repetitively stirring, extracting and concentrating for four times, *Bupleurum scorzonerifolium* acetone crude extract (BS-AE) is obtained and filtered to yield BS-AE residues. The residues are extracted again in methanol to obtain *Bupleurum scorzonerifolium* methanol crude extract (BS-ME) whose residues are further extracted in water to obtain *Bupleurum scorzonerifolium* water extract (BS-WE). Subsequently, BS-AE is dissolved in methanol aqueous solution and isolated using n-Hexane solution to obtain *Bupleurum scorzonerifolium* n-hexane extract (BS-HE) and Bupleurum scorzonerifolium methanol water extract. The methanol in *Bupleurum scorzonerifolium* methanol water extract is removed before the *Bupleurum scorzonerifolium* methanol water extract (BS-MWE) is subjected to repetitive extraction and concentration in chloroform to obtain *Bupleurum scorzonerifolium* chloroform extract (BS-CE). Chromatography based method is then utilised to isolate the BS-CE and collect individual fractions after each methanol/dichloromethane elution. Lastly, chromatographic method (such as silica gel chromatography or preparative HPLC) is used to isolate and purify active methanol/dichloromethane elution fraction, in order to obtain active pure compounds.

The molecular mass and structure of the pure compounds isolated from chromatography are identified using mass spectrometry and nuclear magnetic resource spectrometry. The resultant heterocyclic compounds are tabulated as follows:

| Isolated Component | Structure Formulae | Molecular weight and structure |
|---|---|---|
| Component 1 | 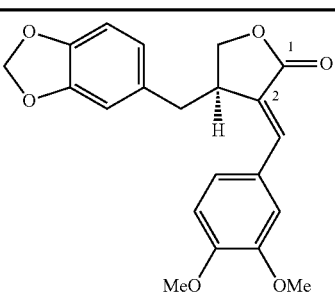 | 368.39 Kaerophyllin |

-continued

| Isolated Component | Structure Formulae | Molecular weight and structure |
|---|---|---|
| Component 2 | | 398.41<br>Yatein |
| Component 3 | | 398.41<br>Chaihulactone |
| Component 4 | | 284.27<br>Oroxylin A |
| Component 5 | | 284.27<br>Wogonin |
| Component 6 | | 380.35<br>Chinensinaphthone |
| Component 7 | | 316.31<br>1,2,3,7-tetramethoxanthone |

-continued

| Isolated Component | Structure Formulae | Molecular weight and structure |
|---|---|---|
| Component 8 | | 398.41 Isochaihulactone |
| Component 9 | | 206.20 Eugenin |
| Component 10 | | 222.20 Saikochromone A |
| Component 12 | | 300.27 Isoscutellarein-8-methyl ether |
| Component 14 | | 394.38 Chaihunaphthone |
| Component 15 | | 368.39 Isokaerophyllin |

The variety of *Bupleurum scorzonerifolium* extracts obtained and the aforementioned heterocyclic compounds isolated from the acetone crude extracts of *Bupleurum scorzonerifolium* are subjected to drug screening test to determine that majority of tumor inhibitory components of *Bupleurum scorzonerifolium* lies in the BS-AE and BS-ME. Besides, the extracts can be further purified using chromatographic method (e.g. low pressure liquid chromatography or high performance liquid chromatography (HPLC)), such that different fractions are collected separately after each elution, which fractions are concentrated to obtain the pure compounds mentioned above.

From the results obtained from the drug screening test of the preferred embodiment of the invention, among those components isolated using chromatographic method, the third and eighth components have the most prominent cytotoxic effects on human hepatoma, lung cancer, ovarian cancer, malignant glioblastoma and colorectal cancer.

Moreover, from chemical analysis of the main representative molecular structure of the third and eighth components, it was observed that the compounds having the tumor inhibitory effects are heterocyclic compounds and pharmaceutical composition thereof having a γ-butyrolactone core and a Z configuration or E configuration for its carbon 2(5) location as illustrated in formula (I).

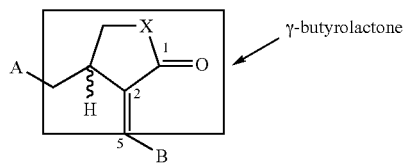

Formula (I)

where, X=N, O, S, or Se; and A, B can be selected from the following substituents:

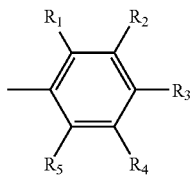

where R1, R2, R3, R4, R5 can be selected from hydrogen atom, a halogen atom, a hydroxyl group, a mercapto group, an amino group, an alkoxy group, and a nitro group.

When the third, eighth, fourteenth and fifteenth components are further analysed for their molecular structures, it is found a novel group of heterocyclic compounds are present in *Bupleurum scorzonerifolium* extracts. These novel heterocyclic compounds are published for the first time and are named as Chaihulactone, Isochaihulactone and Chaihulactone-related analogues or derivatives, such as Chaihunaphthone. And among these compounds, the chaihulactone and isochaihulactone are both γ-butyrolactone centered heterocyclic compounds and have Z-configuration for their carbon 2(5) location. The formulae of chaihulactone analogues and isochaihulactone analogues are shown by Formula II and Formula III, respectively:

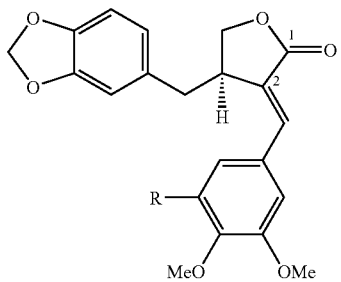

Formulae (II)

wherein R represents an alkoxy group.

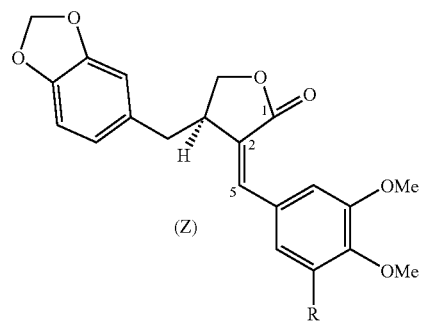

Formulae (III)

wherein R represents hydrogen atom, an alkoxy group, or an aromatic group.

These novel heterocyclic compounds, i.e. Chaihulactone, Isochaihulactone and Chaihulactone analogues or derivatives, belong to a kind of lignan, which is present in crude *Bupleurum scorzonerifolium*. Since it was found that BS-AE and isochaihulactone have the most significant tumor-suppressing effects among all those types of *Bupleurum scorzonerifolium* extracts described above. Therefore, the BS-AE and isochaihulactone are used as index for assessing in vivo and in vitro tumor inhibitory effects of the above-mentioned extracts on human hepatoma, ovarian cancer, lung cancer, malignant glioblastoma and colorectal carcinoma.

From results of the histological section according to the preferred embodiments of the invention, it clearly indicated that BS-AE could effectively reduce tumor volume, induce nuclear fragmentation for tumor cell and lymphocyte infiltration, and result in a large area of necrosis of tumor tissue. Moreover, from the results of toxicity test on animals, the mammalian models do not show significance differences in terms of internal organ functionality indicators, such as lipase, amylase, creatinine kinase, lactate dehydrogenase, GOT, BUN before or after BS-AE containing the γ-butyrolactone compound and pharmaceutical composition thereof is applied to mammalian models. However, the telomerase activity of the tumor cell was decreased significantly after application of BS-AE. Thus, it is demonstrated that administration of the γ-butyrolactone compound and pharmaceutical composition thereof on mammals could exert highly specific cytotoxicity to human hepatoma, ovarian cancer, lung cancer, malignant glioblastoma and colorectal cancer without damaging normal liver and kidney functions.

On the other hand, when the representative component "BS-AE" of the γ-butyrolactone compound and pharmaceutical composition thereof is applied on Paclitaxel-resistant tumor cell line, for example, human lung cancer cell line A549-T12 to observe their tumor inhibitory effect, it was found that following the isolation and purification steps, the effective concentration (about 1.2 μg/mL) of isochaihulactone for inhibiting telomerase activity of the Paclitaxel-resistant tumor cells is much smaller than the effective concentration of (about 60 μg/mL). Furthermore, after crude Bupleurum scorzonerifolium is processed according to the above-mentioned manufacturing method, its tumor inhibitory effect is more prominent.

Moreover, the γ-butyrolactone compound and pharmaceutical composition thereof are similar to Paclitaxel in terms of their mechanisms, as they both act as a microtubule stabilizing agent to repress mitosis in a similar manner as paclitaxel. However, these two drugs may target on different parts of β-tubulin.

In summary, the novel γ-butyrolactone compound and pharmaceutical composition thereof, such as "chaihulactone, isochaihulactone, and their derivatives," once isolated from Bupleurum scorzonerifolium could potentially become source for the new anti-tumor drugs.

This invention will be explained in detailed with the following embodiments which is not intended to limit the scope of this invention.

PREFERRED EMBODIMENTS

The present invention will be explained in detail with all the tables and figures on the following subjects: (1) a method for manufacturing Bupleurum scorzonerifolium extracts, (2) the γ-butyrolactone compound and pharmaceutical composition thereof isolated from Bupleurum scorzonerifolium extract to have tumor-inhibitory effect, and (3) the preferred embodiments of methods for treating human hepatoma, ovarian cancer, lung cancer, malignant glioblastoma and colorectal carcinoma and other cancer cells with the γ-butyrolactone compound and pharmaceutical composition thereof. The following embodiments are meant to provide the best modes for carrying out the present invention, rather than to limit the scope of the invention to the disclosed embodiments. And when Bupleurum scorzonerifolium extracts and their active components are made into pharmacologically compatible salts, esters, ketones or analogues, the composition, formulation, and synthesizing method thereof can be adjusted according to the practical circumstances.

First Embodiment

Extraction Method of Antineoplastic Extracts and Compounds from Bupleurum scorzonerifolium Bupleurum scorzonerifolium used in this invention is radix Bupleuri of Umbelliferae family. After drying and grinding of the Buleurum scorzonerifolium plant tissue, 6 kg of Bupleurum scorzonerifolium powder is submerged and stirred within 20 L acetone at room temperature for 4 hours and extracted 4 times repeatedly to obtain the Bupleurum scorzonerifolium-acetone crude extract (BS-AE). Methanol is added to the residues to obtain Bupleurum scorzonerifolium-methanol extract (BS-ME). Then water is added to the residue to obtain Bupleurum scorzonerifolium-water extract (BS-WE). Then 95% methanol solvent is used to dissolve BS-AE, followed by partitioning with n-hexane for 3 times so as to isolate Bupleurum scorzonerifolium-hexane extract (BS-HE) and Bupleurum scorzonerifolium-methanol water extract (BS-MWE). 500 ml of distilled water is then added to the BS-MWE to remove the methanol therein. Next, chloroform is further added to the BS-MWE free of methanol to carry out extraction. After extracting with chloroform for 3 times, chloroform and water are isolated and concentrated to produce Bupleurum scorzonerifolium-chloroform extract (BS-CE).

MTT assay is used to test the cytotoxic effect of BS-AE, BS-ME, BS-HE, BS-CE and BS-WE on human lung cancer cell line A549. Table 1 shows that extracts from BS-AE and BS-CE have the best tumor inhibitory effect among all Bupleurum scorzonerifolium extracts. According to the extraction process "BS-AE→BS-MWE→BS-CE" all of the crude extracts contain tumor inhibitory components. In order to further isolate the tumor inhibitory components from Bupleurum scorzonerifolium extract, a "Chromatography" step is further employed to isolate the BS-CE.

A Silica Gel Chromatography is employed to elute 100 g BS-CE with 5% methanol/dichloromethane, 10% methanol/dichloromethane, 20% methanol/dichloromethane and methanol to obtain 27.5 g of 5% methanol/dichloromethane, 14.04 g of 10% methanol/dichloromethane, 10.96 g of 20% methanol/dichloromethane and 7.25 g of extract respectively. The tumor inhibitory components are retained mainly in the 5% methanol/dichloromethane extract. Then, preparative High Performance Liquid Chromatography (HPLC), Medium Pressure Liquid Chromatography (MPLC), Lobar, and other chromatographic methods are employed to isolate the 5% methanol/dichloromethane extract, as well as to further collect by concentrating the third, eighth, fourteenth and fifteenth components having tumor inhibitory effects.

Second Embodiment

Structure of Active Tumor Inhibitory Component in Buplerum scorzonerifolium

Mass Spectrum and Nuclear Magnetic Resonance Spectrum (NMR) are employed to determine the molecular weight and structure of the third, eighth, fourteenth and fifteenth components isolated from the BS-AE, the mass spectrum is shown in the table 2 below:

TABLE 2 the components isolated from the antineoplastic compounds in BS-AE

| Low pressure liquid chromatography | Structure formulae | Molecular weight and structure |
|---|---|---|
| Component 3 | 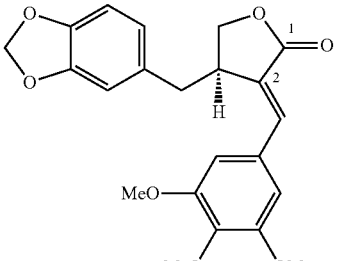 | 398.41 Chaihulactone |

TABLE 2-continued the components isolated from the antineoplastic compounds in BS-AE

| Low pressure liquid chromatography | Structure formulae | Molecular weight and structure |
|---|---|---|
| Component 8 | | 398.41 Isochaihulactone |
| Component 14 | | Chaihunaphthone |
| Component 15 | | Isokaeophyllin |

After analyzing the molecular structures, it is appreciated that the pure compounds isolated from *Bupleurum scorzonerifolium* having inhibitory effect on tumor cells of human hepatoma, ovarian cancer, lung cancer, malignant glioblastoma and colorectal carcinoma are heterocyclic compounds having a γ-butyrolactone core, and Z or E configuration for its carbon 2(5) location. From the cytotoxicity test, it was found that the third and eighth components show better cytotoxic effects than other components on the lung cancer cell lines. Therefore hydrogen-nuclear magnetic resonance ($^1$H-NMR) and carbon 13-nuclear magnetic resonance ($^{13}$C-NMR) are used to further analyze the molecular structures of the crystallized structure of the third and eighth components, to obtain two novel compounds "chaihulactone" and "isochaihulactone" which are shown as formulae I and II.

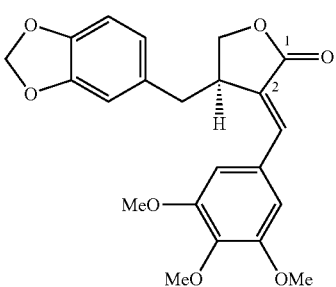

Formula (I)

Formula (II)

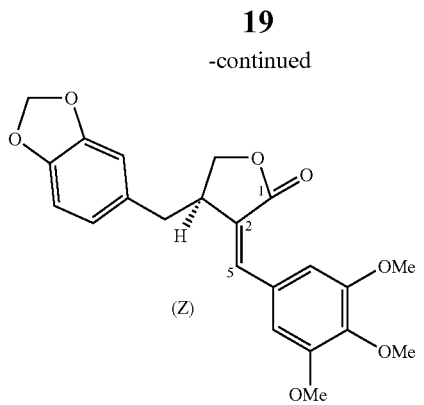

(Z)

(white needle crystal, melting point of 137-138° C.$[\alpha]_D^{25}$ −29.0° (c0.5, CHCl3); IR (KBr) $\nu_{max}$ cm$^{-1}$: 1745, 1635, 1581, 1335, 1153; UV (CHCl3) $\lambda_{max}$ nm (log ε): 247(4.08), 298 (4.17), 327(4.08))

In addition, other compounds having tumor inhibitory effects, for example the representative molecules of the first, second, eleventh, and fifteenth components and their analogues or derivatives are analyzed and compared with current pharmaceutical database. The result of the comparison indicates that the pharmaceutical compositions of *Bupleurum scorzonerifolium* showing cytotoxic effect on tumors are heterocyclic compounds containing γ-butyrolactone as a core structure, and Z configuration or E configuration for its carbon position 2(5). The formula (I) of the heterocyclic compounds is listed as follows:

Formula (I)

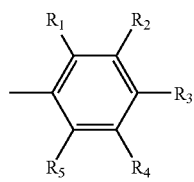 γ-butyrolactone wherein X=N, O, S, or Se; and A, B can be selected from the following substituents:

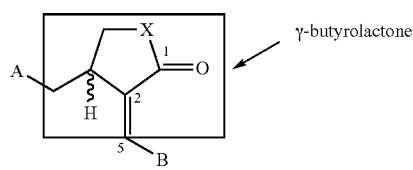

wherein R1, R2, R3, R4, R5 can be selected from a hydrogen atom, a halogen atom, a hydroxyl group, a mercapto group, an amino group, an alkoxy group, and a nitro group and the substituents further comprise the following structures:

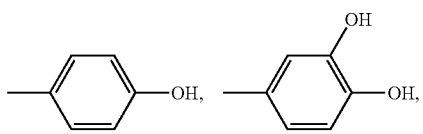

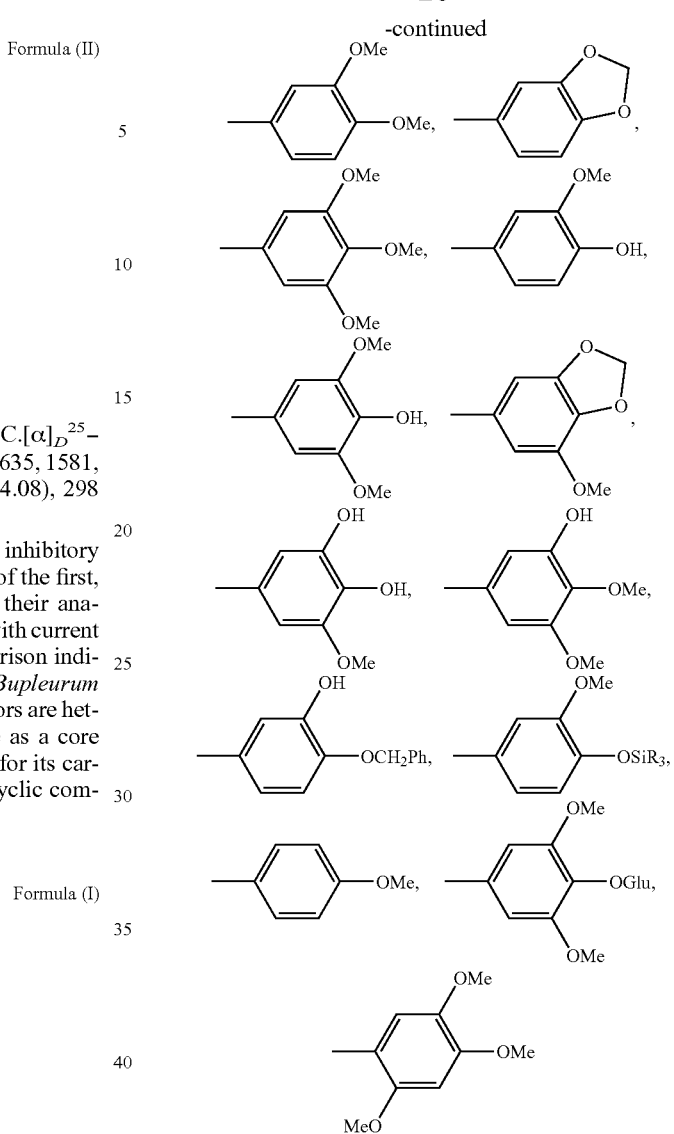

The evaluation of the cytotoxicity shows that the eighth component isochaihulactone elicits more prominent cytotoxic effect than other chaihulactone analogs on lung cancer cell line. Therefore, the following embodiments are described using the BS-AE and isochaihulactone (BS-(8)) as representative substances to evaluate the efficacy of γ-butyrolactone compound and pharmaceutical composition thereof.

Third Embodiment

The Effect of *Bupleurum scorzonerifolium* Extracts on Cell Proliferation

BS-AE, BS-ME and BS-8 are added to cell cultures of J5, Ovcar-3. A549, DBTRG-05, and HT-29, respectively to observe growth inhibition of the cancer cell lines during the 7 days treatment. The present embodiment is described with lung cancer cell line A549 and colon cancer cell line HT-29 as examples. It was found that the cancer cell lines administered with 60 μg of BS-AE had their tumor cell counts reduced to a similar level as the cancer cell lines administered with 600 μg of BS-ME three days after the extracts were given, indicating that the tumor inhibitory component in BS-ME is much lower than that in BS-AE. Therefore it is concluded that the most effective tumor inhibitory compounds from *Bupleurum scorzonerifolium* are mainly present in BS-AE.

Figure 2B:
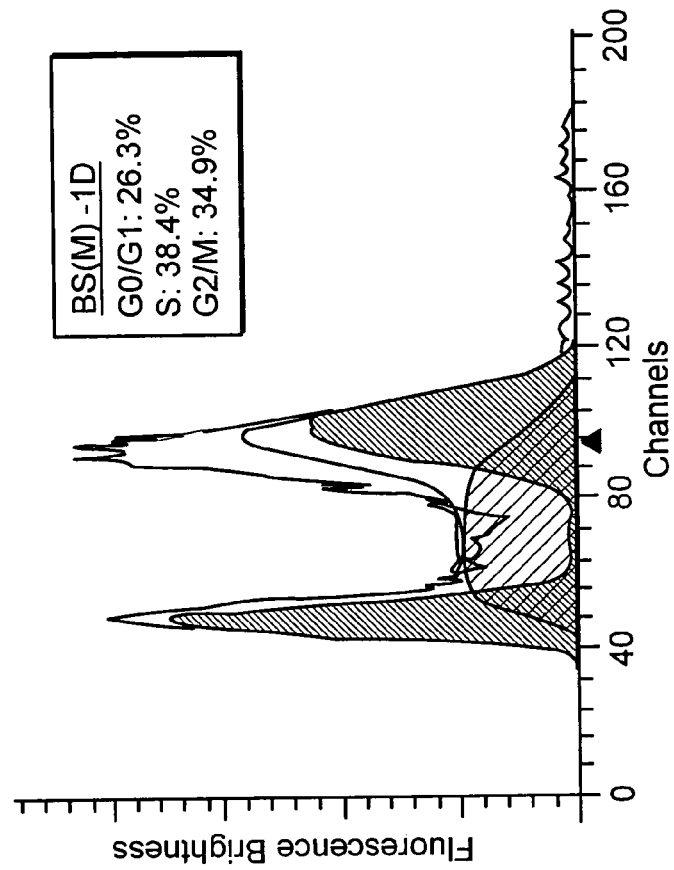
FIGS. 2A through to FIG. 2D illustrate the cell cycle peak change detected using flow cytometry for A549 cells treated with *Bupleurum scorzonerifolium* extracts: acetone extract (BS-AE), methanol extract (BS-ME) and water extract (BS-WE) isolated according to the extracting method of the invention.
Figure 2A:
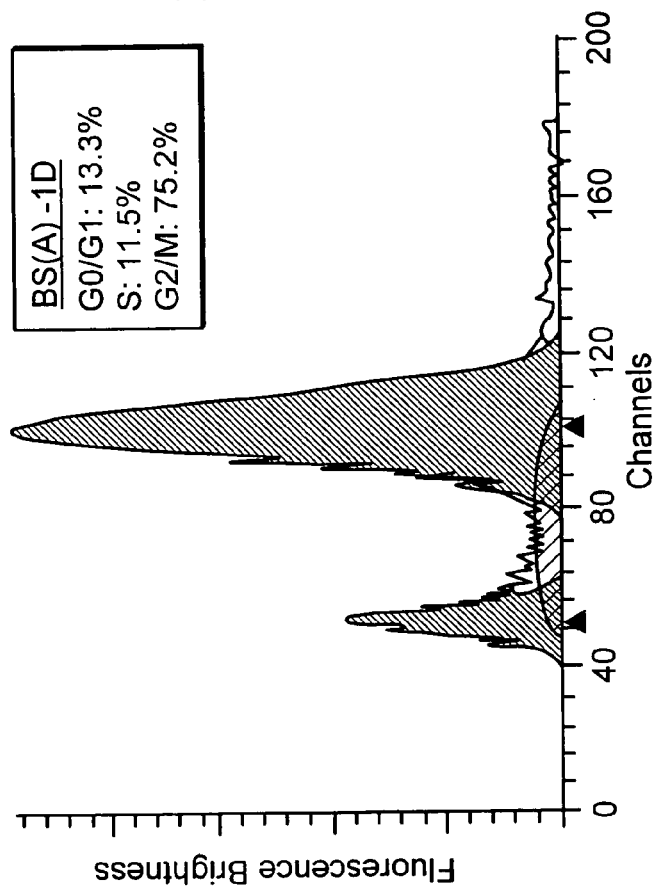

Furthermore, flow cytometry is employed to observe the changes in cell cycle before and after the addition of different extracts from *Bupleurum scorzonerifolium* to A549 cells. In FIGS. 2A through to 2D, X-axis represents chromosome numbers (2N, 4N, etc.) of tumor cells in contact with the antibody, Y-axis represents the fluorescent brightness of Fluorescein Isothiocyanate (FITC). It is clearly noted that lung cancer cell line A549 is mainly distributed at G0/G1 stage before treatment, but when BS-AE and BS-ME are added to the tumor cells, the tumor cells are arrested at G2/M stage. This effect is most significant for BS-AE. On the other hand, from the Propidium Iodide (PI) staining result of the flow cytometry, it was also found that the chromosome at G0/G1 stage is reduced in number after adding the *Bupleurum scorzonerifolium* extract, bur the chromosome (2N, 4N and so on) at G2/M stage is significantly increased in number. And the same effects are also seen in human hepatoma cell lines, ovarian cancer cell lines, lung cancer cell lines and colorectal cancer cell lines, suggesting the tumor inhibition mechanism of the γ-butyrolactone compound and pharmaceutical composition thereof is likely related to cell arrest at G2/M stage of the cell cycle.

Fourth Embodiment

*Bupleurum scorzonerifolium* Extracts and Apoptosis

In order to further prove the putative apoptosis effects of the *Bupleurum scorzonerifolium* extracts on the tumor cell line, flow cytometry, Reverse Transcription Polymerase Chain Reaction (RT-PCR), and Western Blotting analysis are used to monitor any change in tumor cell cycle and change in expression level of the regulatory protein p21 and p53 after tumor cell lines are added with BS-AE and isochaihulcatone.

Figure 3A:
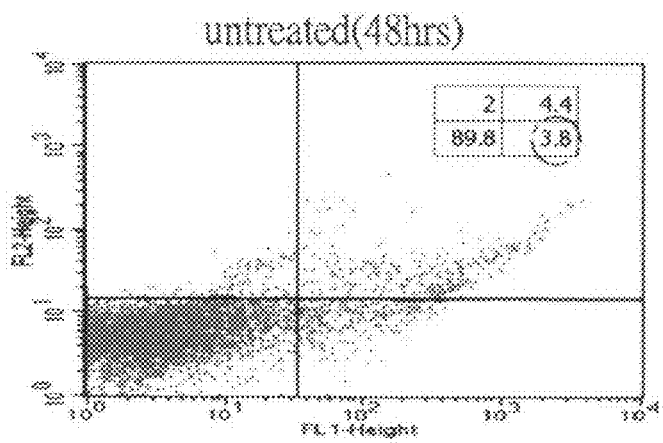
FIGS. 3A through to FIG. 3C are cytograms showing the extent of cell apoptosis detected using flow cytometry for A549 cells either untreated, treated with 20 μM of isochalihulactone, or 60 μg/ml of BS-AE and cultured for 48 hrs (wherein X-axis indicates fluorescence intensity of tumor cells bound with Annexin V-FLOUS antibodies; and Y-axis indicates fluorescence intensity of tumor cells bound with PI antibodies)
Figure 3B:
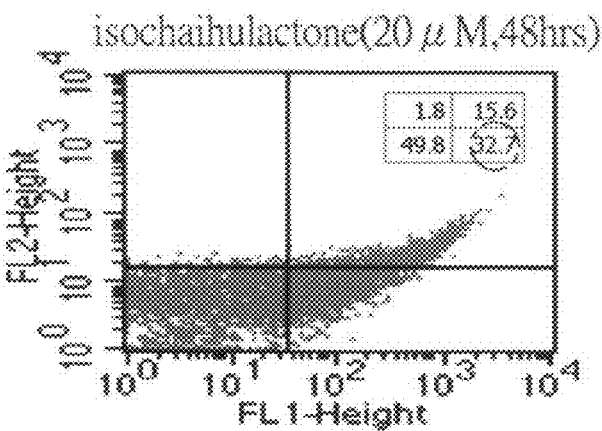
Figure 3C:
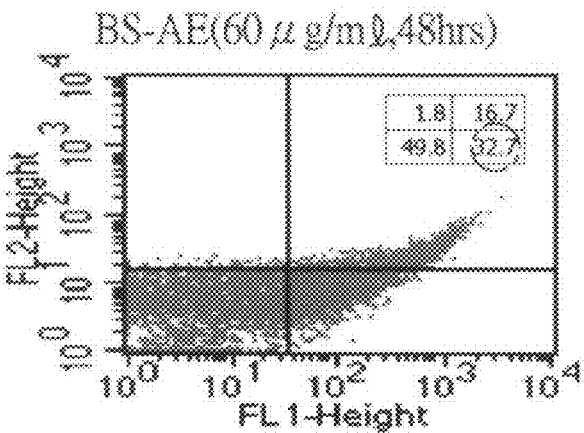

In the example of using cell line A549, untreated A549 cells, A549 cells treated with 2 μM of Isochaihulactone and A549 cells treated with 60 μg/ml of BS-AE are cultured 48 hours before utilizing flow cytometry to detect the staining results between Annexin V-FLOUS and PI. In FIGS. 3A through to 3C, X-axis represents the fluorescent brightness of tumor cells with antibody Annexin V-FLOUS, and Y-axis represents the fluorescent brightness of tumor cells with antibody PI. From the diagrams, it was shown that the untreated group has only 3.8% of cells coupled to Annexin V (showing peel-off of the cell membrane indicating cell apoptosis), whereas A549 cells treated with Isochaihulactone and BS-AE and cultured for 48 hours has significantly increased to 32.7% of the tumor cells coupled to Annexin V. These results strongly suggest the γ-butyrolactone compound and pharmaceutical composition thereof play a role in inducing apoptosis of the tumor cells.

Figure 4:
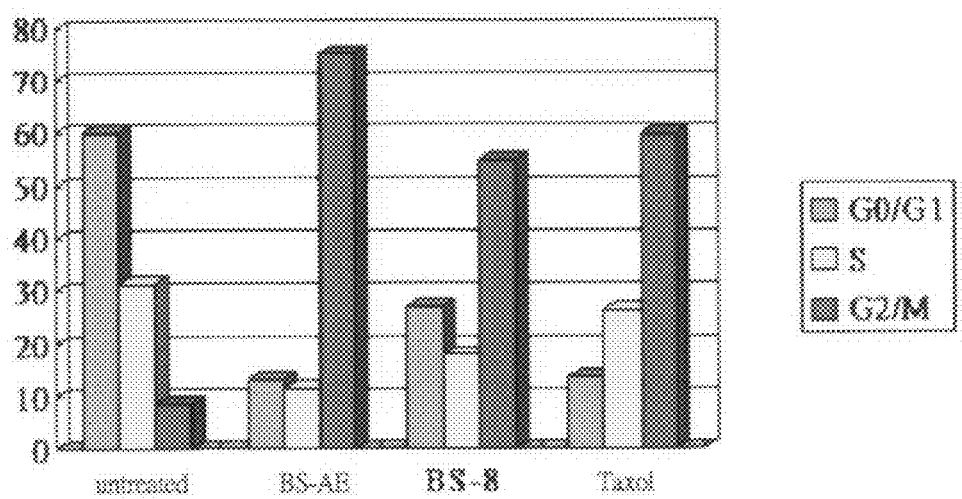
FIG. 4 is a bar chart showing cell cycle changes detected using flow cytometry for A549 cells untreated, treated with BS-AE, isochaihulactone (BS-8), and Paclitaxel.
Figure 5:
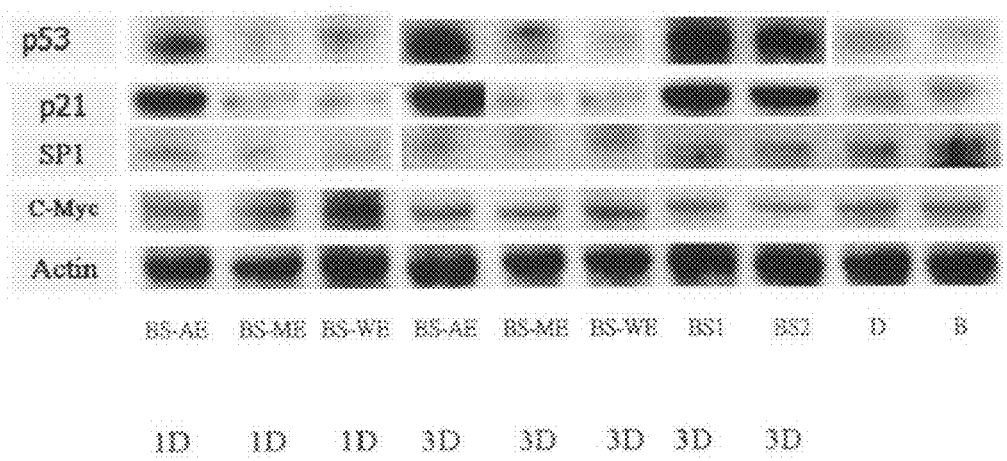
FIG. 5 is a western blot analysis diagram showing the amount of tumor suppressors: p21 and p53 expressed in A549 cells either untreated (B), treated with DMSO (D) or BS-AE, BS-ME, BS-WE, isochaihulactone (BS-1), or chaihulactone (BS-2) for 1 day (1D) or 3 days (3D)

Furthermore, from the Cell Cycle in FIG. 4 and the result of Western Blotting analysis in FIG. 5, it was apparent that BS-AE and isochaihulactone could induce the tumor cells to arrest at G2/M stage in a manner similar to Paclitaxel. Moreover, BS-AE and chaihulactone analogs (such as third and eighth components) result in a significant increase in expression level for tumor suppressor p21 and p53, which interfere with cyclin D and cyclin E, so as to bar the cells from entering G0/G1 stage, causing the tumor cells to arrest at G2/M stage.

Therefore, from the results shown above, it should be apparent that the γ-butyrolactone compound and pharmaceutical composition thereof are effective in arresting the tumor cells at G2/M stage as well as inducing the tumor cells to go into apoptosis. The same effects are also observed in human hepatoma, lung cancer, ovarian cancer, malignant glioblastoma and colorectal carcinoma, suggesting the γ-butyrolactone compound and pharmaceutical composition thereof should have an inhibitory effect on the cell proliferation of human hepatoma, lung cancer, ovarian cancer, malignant glioblastoma and colorectal carcinoma. Thus, the γ-butyrolactone compound and pharmaceutical composition thereof may serve as a G2/M arresting agent having a similar mechanism as Paclitaxel.

Figure 6:
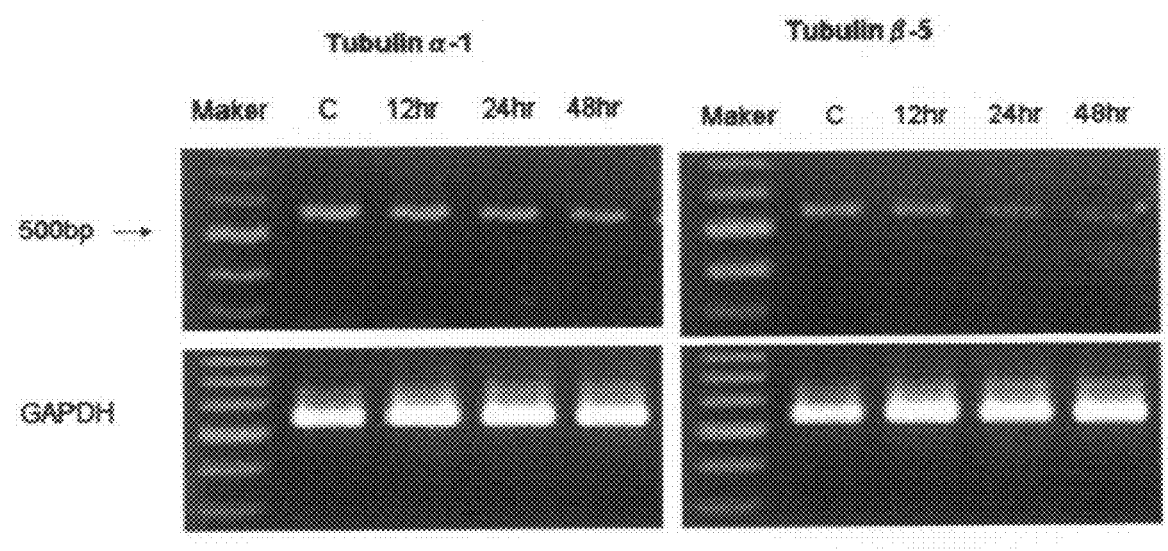
FIG. 6 is a western blot analysis diagram of reverse transcriptase polymerase chain reaction (RT-PCR) showing messenger ribonucleic acid (mRNA) expression of type-1 α tubulin and type-5 β-tubulin in A549 cells either untreated (C), treated with BS-AE for 12 hrs, 24 hrs, and 48 hrs.
Figure 7:
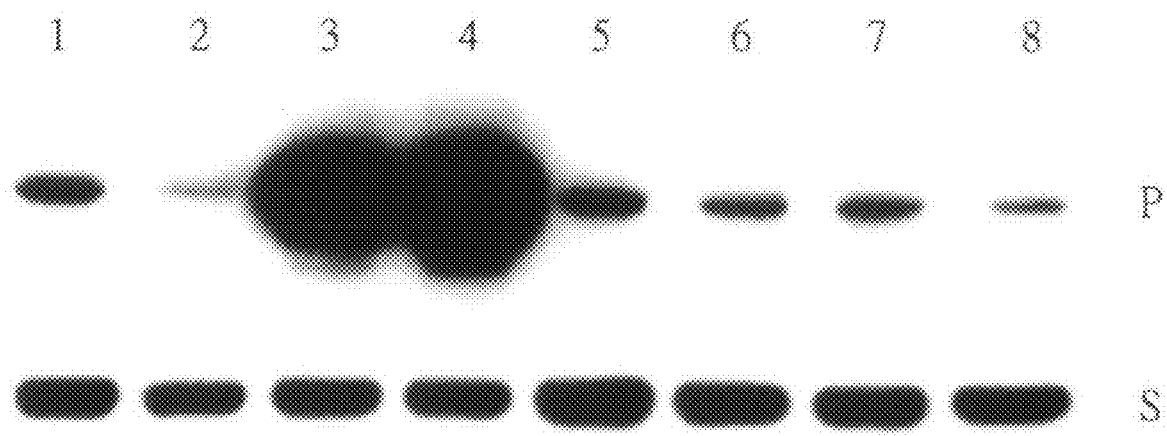
FIG. 7 is a western blot analysis diagram showing expression of soluble (S) and particular (P) form of β-tubulin in A549 cells either untreated (C), treated with BS-AE, isochaihulactone (BS-8), Paclitaxel, or Vinblastine.

Reverse transcriptase polymerase chain reaction (RT-PCR) is then used to analyze the change of cytoskeleton of tumor cell lines treated with *Bupleurum scorzonerifolium* extract. As shown in FIG. 6, the cytoskeleton of type-I α-microtubule has no significant change after treating A549 cells with BS-AE for 12, 24 and 48 hrs. Instead, a gradual decrease in the number of type-V β-microtubule is detected. Then, a polymerization event is observed before and after the treatment of BS-AE. As shown in FIG. 7, after isochaihulactone, the soluble form (non-polymerized β-microtubule illustrated as S in the diagram) significantly diminishes, whereas the particular form (polymerized β-microtubule illustrated as P in the diagram) increases. This indicates that the γ-butyrolactone compound and pharmaceutical composition thereof have similar effect on the polymerization of β-tubulin as Paclitaxel.

Figure 8:
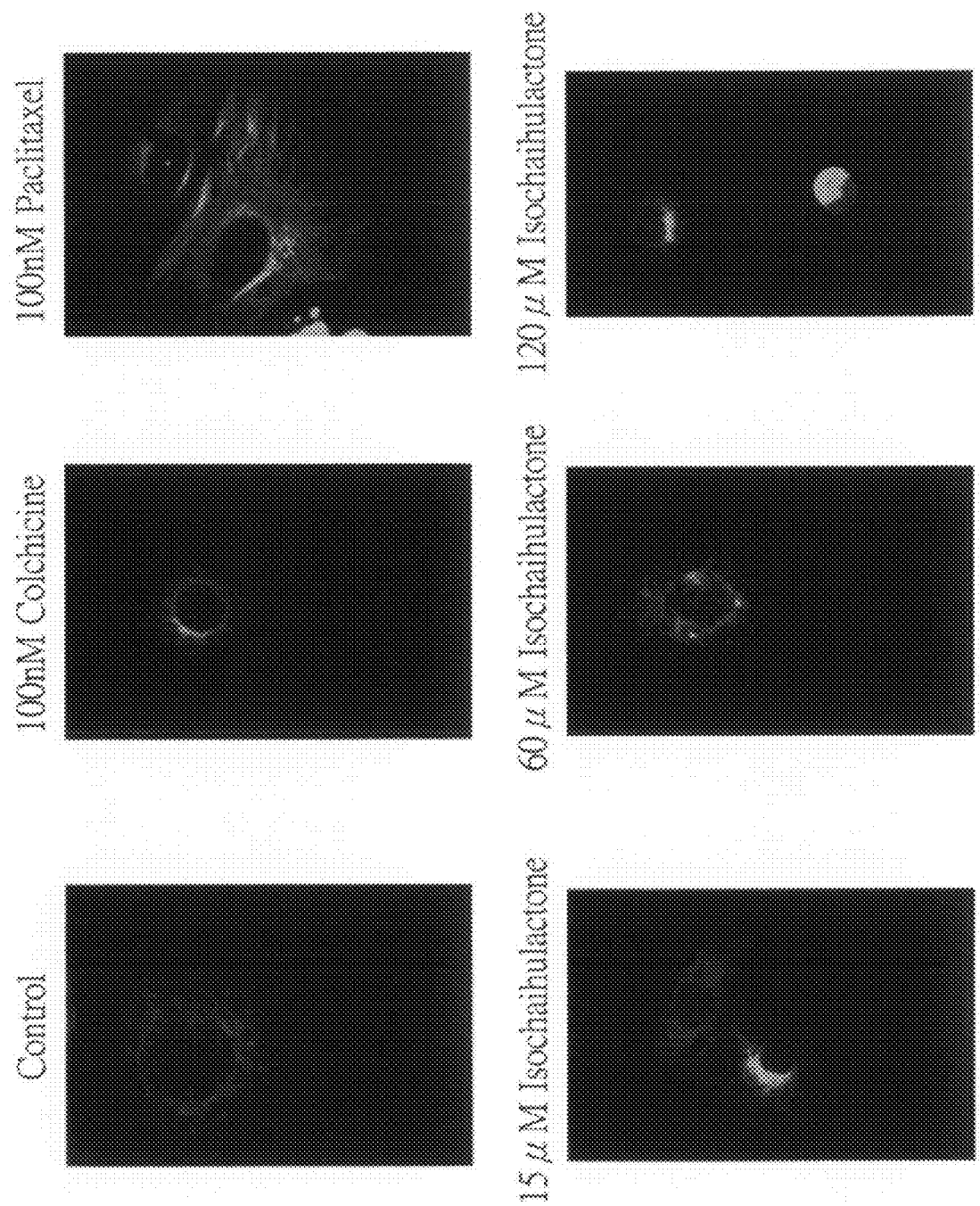
FIG. 8 is a confocal microscopic section showing elongation of spindles in the fluorescent labeled A549 cells treated with BS-AE.

Moreover, confocal microscopy is utilized to further analyze the arrangement of the spindle inside the cytoskeleton of the fluorescent-labeled microtubule. As shown in FIG. 8, after treatment of BS-AE to the tumor cells, the polymerization of β-tubulin results in the progressive elongation of spindle. Therefore, 2N or nN chromosomes are stopped from migrating towards the spindle poles and divisions of tumor cells are inhibited. In this way, tumor cells cannot progress through mitosis successfully with accumulation of 2N and 4N chromosomes, resulting in apoptosis of junk cells.

Fifth Embodiment

The Effect of *Bupleurum scorzonerifolium* Extracts on Paclitaxelresistant Tumor Cell Line Recent cell culture study shows no satisfactory cytotoxic effect on Paclitaxel-resistant tumor cell at late stage of chemotherapy in vitro. The previous results from flow cytometry show that BS-AE and isochaihulactone representing chaihulactone and derivatives thereof and Paclitaxel have similar tumor inhibition mechanism for human hepatoma, lung cancer, ovarian cancer, malignant glioblastoma and colorectal carcinoma. Therefore, the Bupleurum scorzonerifolium extracts serve as a source for screening new drugs to further examine the cytotoxic effect of *Bupleurum scorzonerifolium* extracts on Paclitaxel-resistant tumor cell line.

The following embodiments are described with Paclitaxel-resistant tumor cell A549-T12 (passage cultured from lung cancer cell line A549 cells with low concentration of Paclitaxel) as an example to test the effect of BS-AE and its pure compounds BS-8 and BS-15 (these represent isochaihulactone and chaihulactone analogues) on A549-T12 cells. Flow cytometry, drug toxicity test, and histological sections are adopted to evaluate cytotoxic effect of the γ-butyrolactone compound and pharmaceutical composition thereof on Paclitaxel-resistant tumor cells.

Figure 9A:
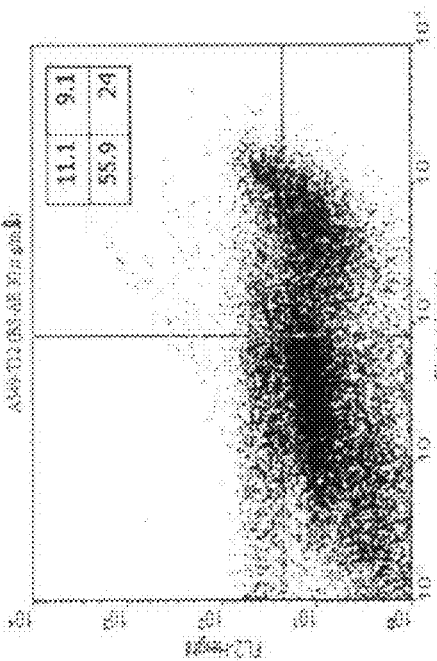
FIGS. 9A through to 9D are cytograms showing the extent of cell apoptosis detected using flow cytometry for Paclitaxel-resistant human lung cancer cell lines (A549-T12 cells) either untreated, treated with BS-AE, isochalihulactone (BS-8), or isokaerophyllin (BS-15) for 24 hrs (wherein X-axis indicates fluorescence intensity of tumor cells bound with Annexin V-FLOUS antibodies; and Y-axis indicates fluorescence intensity of tumor cells bound with PI antibodies)
Figure 9B:
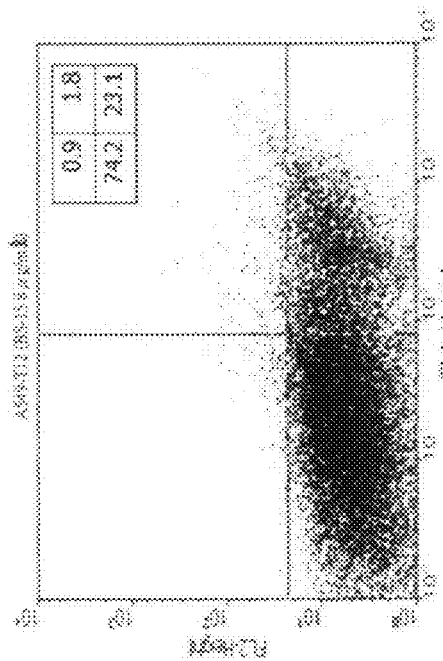
Figure 9C:
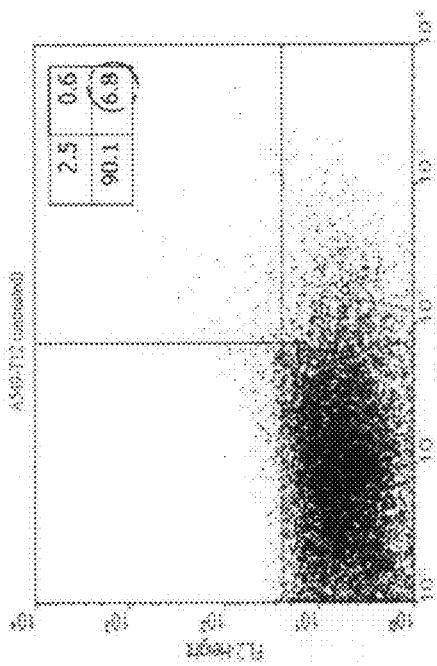
Figure 9D:
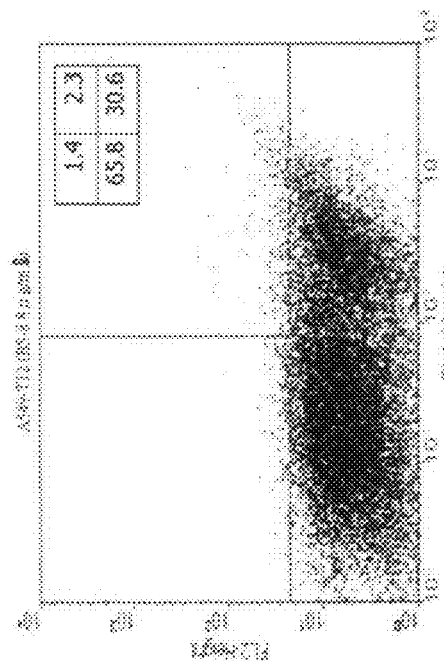

FIGS. 9A through to 9D are flow cytometry results illustrating a comparison of the change of Annexin V-FLOUS and PI for untreated group with that of the group treated with 100 nM of Paclitaxel, 30 μg/ml BS-AE, 8 μg/ml BS-8 and 8 μg/ml BS-15 to A549-T12. Among these figures, X-axis represents the fluorescent brightness of tumor cells with antibody Annexin V-FLOUS whereas Y-axis represents the fluorescent brightness of tumor cell with antibody PI. The result shows that after 48 hours of treatment, only 6.8% of the cells in the untreated group are coupled to Annexin V. However, after the A549-T12 cell line is treated with isochaihulactone, chaihulactone analogues or BS-AE and cultured for 48 hours, the ratios increase to 30.6%, 23.1% and 24% of the tumor cells coupled to Annexin V respectively. This indicates isochaihulactone has better induction for apoptosis of Paclitaxel-resistant tumor cell line than other chaihulactone analogues. Furthermore, BS-AE is more effective for tumor cell apoptosis than crude extracts after purification. Therefore, it is evident that the γ-butyrolactone compound and pharmaceutical composition thereof are active components cytotoxic to the tumor cells.

Figure 10A:
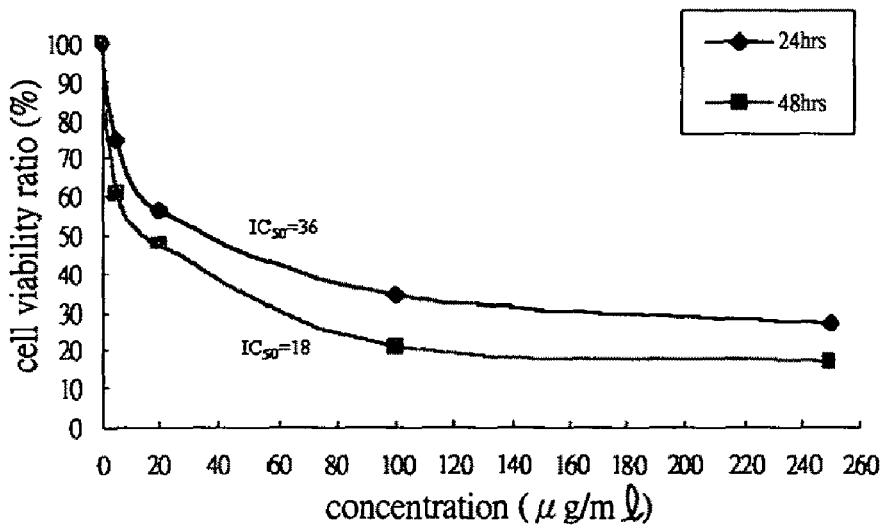
FIGS. 10A through to 10C illustrate results of MTT assays for A549-T12 cells treated with BS-AE, isochaihulactone (BS-8), and isokaerophyllin (BS-15) respectively for 24 hrs and 48 hrs.
Figure 10B:
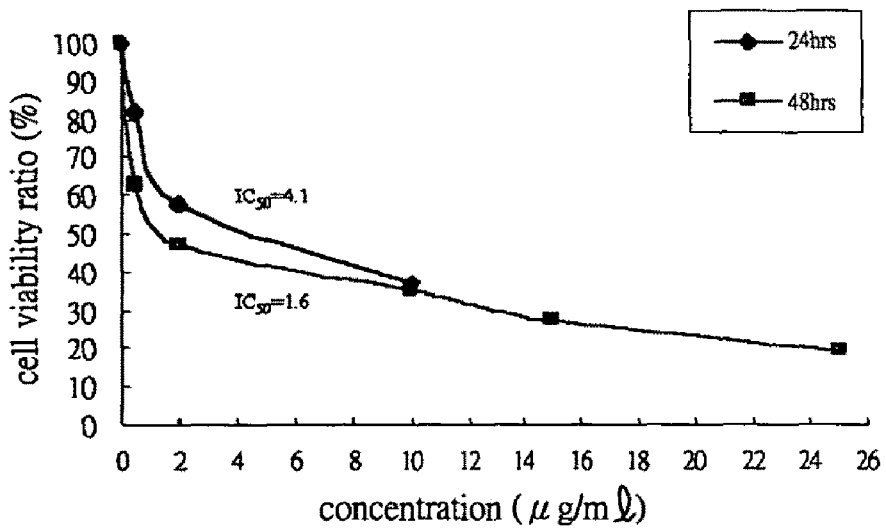
Figure 10C:
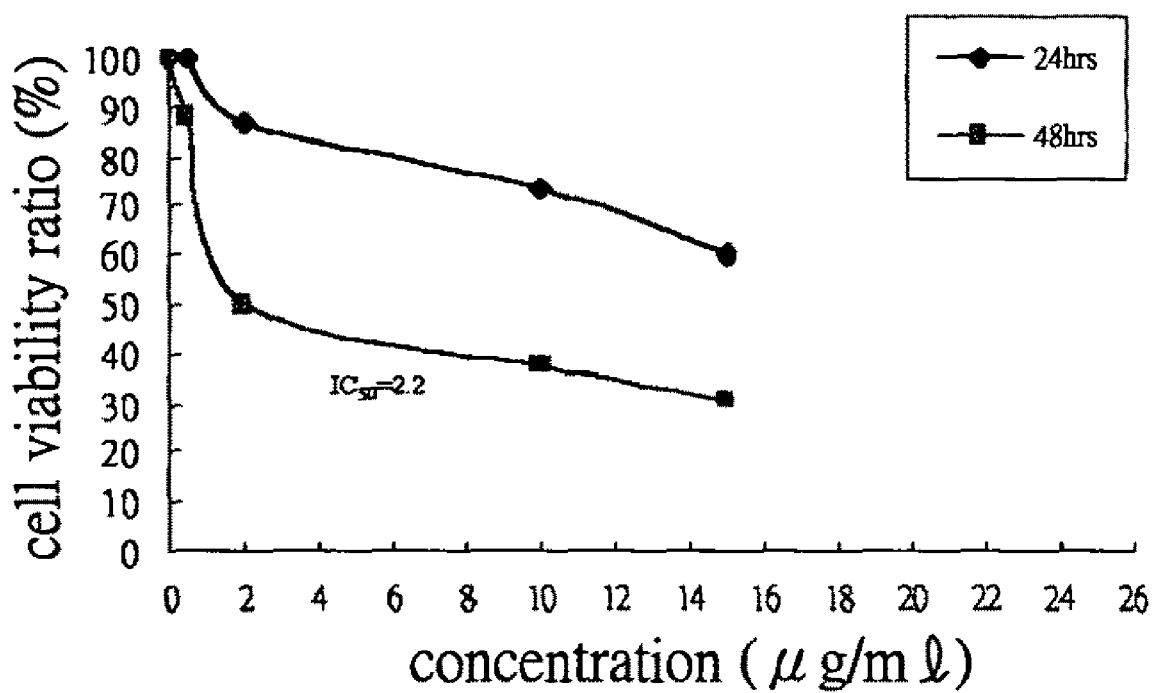
Figure 11A:
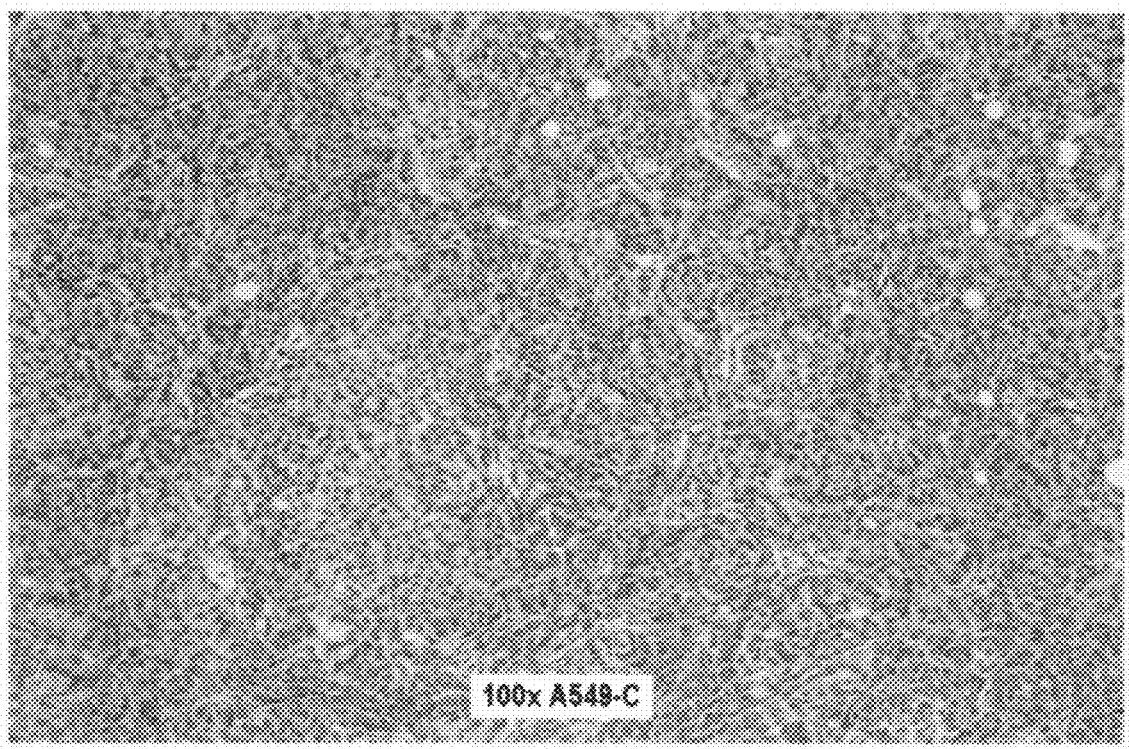
FIG. 11A is a histological section of mouse subcutaneous tumor tissue inoculated with A549 tumor cells, the section is stained with haematoxylin and eosin stain (H&E stain) and observed with a 100 times magnification.
Figure 11B:
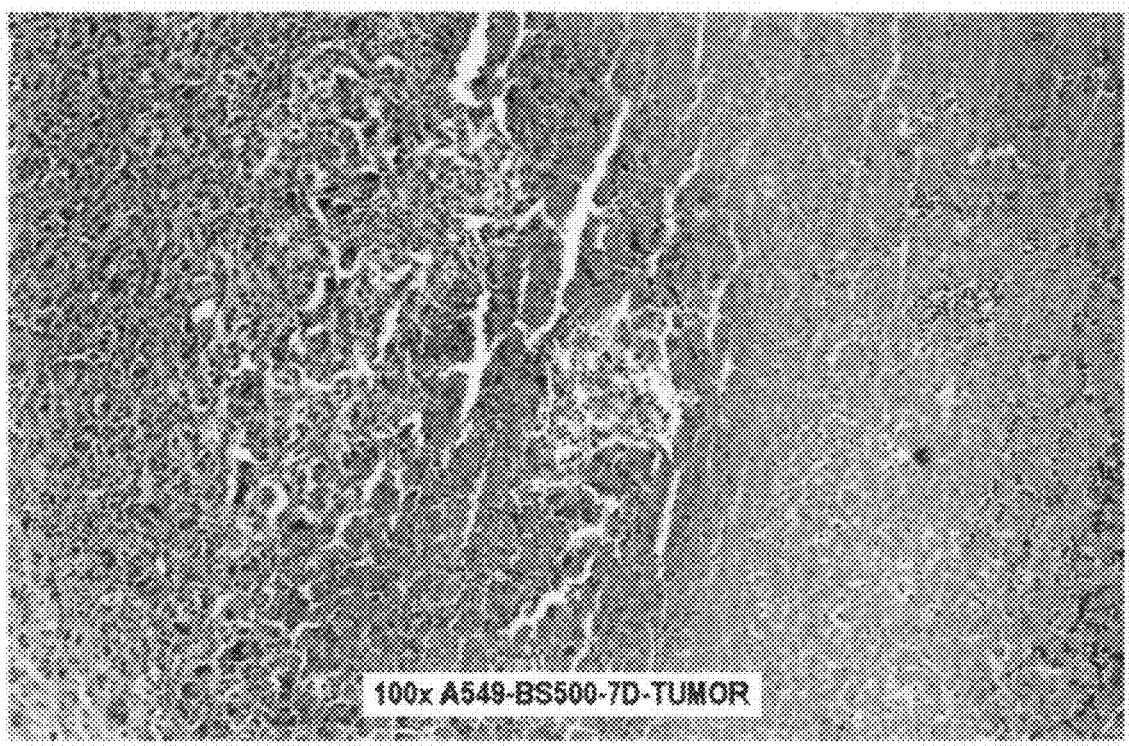
FIG. 11B is a histological section showing a large area of necrosis for tumor cells taken from the mouse subcutaneous tumor tissue inoculated with A549 tumor cells one week after intraperitoneal (I.P.) administration of 500 mg/kg of BS-AE for 5 consecutive days.

Besides, after BS-AE, BS-8, and BS-15 are added to Paclitaxel-resistant lung cancer cell line for 48 hours, viability ratio of tumor cells is reduced as illustrated in FIGS. 10A through to 10C. So, in view of $IC_{50}$ or $ED_{50}$, the cytotoxic effect of purified chaihulactone analog on the tumor cells is weaker than BS-AE. It demonstrates that chaihulacetone, isochaihulactone, and their derivatives are indeed the main active in *Bupleurum scorzonerifolium* for inhibiting tumors. Furthermore, a substantially low dose (1.5 μg/ml) of the compound is all that requires to induce apoptosis for the tumor cells.

Sixth Embodiment

Figure 12A:
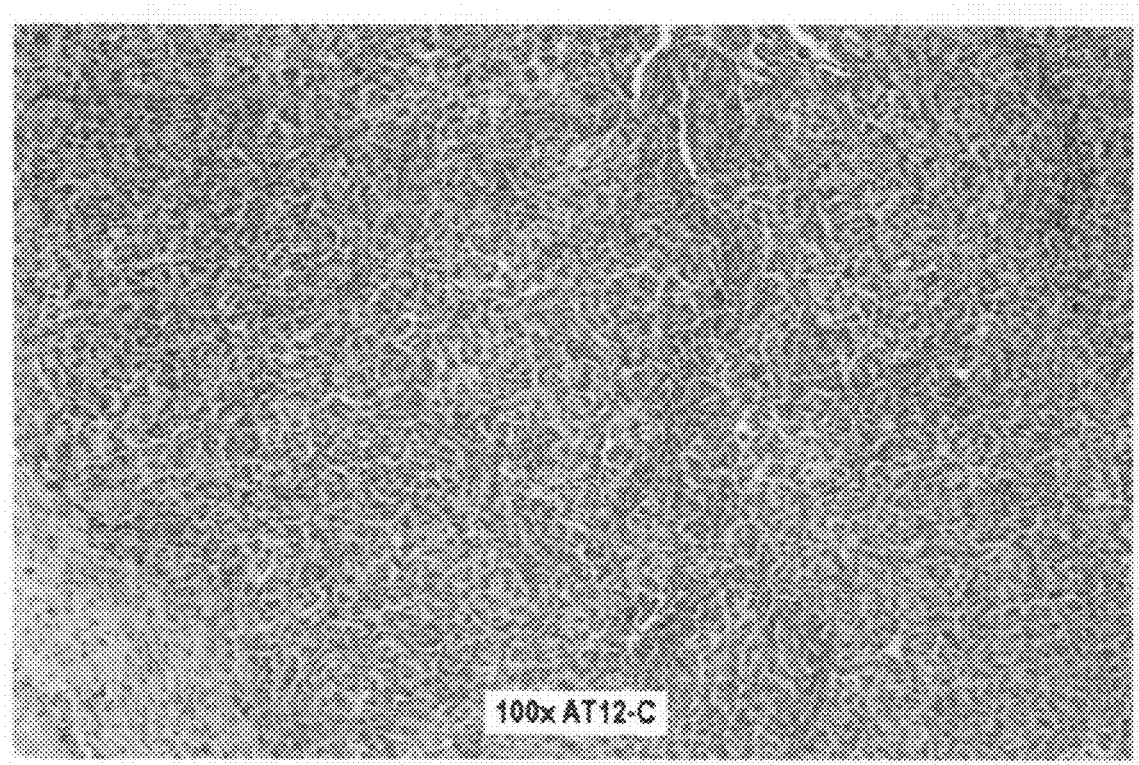
FIG. 12A is a histological section of mouse subcutaneous tissue inoculated with A549-T12 tumor cells, the section is stained with haematoxylin and eosin stain (H&E stain) and observed with a 100 times magnification.
Figure 12B:
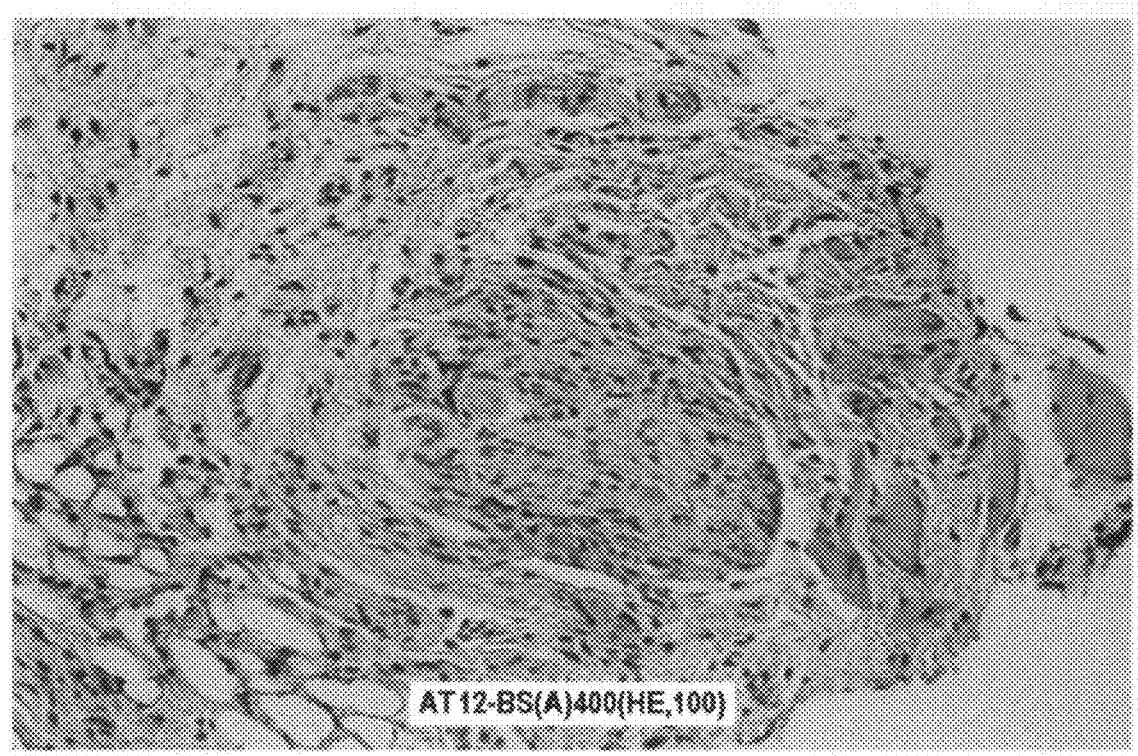
FIG. 12B is a histological section showing a large area of tissue fibrosis and only a small proportion of residual tumor cells, taken from mouse subcutaneous tumor tissue inoculated with A549-T12 tumor cells one week after I.P. administration of 400 mg/kg of BS-AE for 5 consecutive days.
Figure 13A:
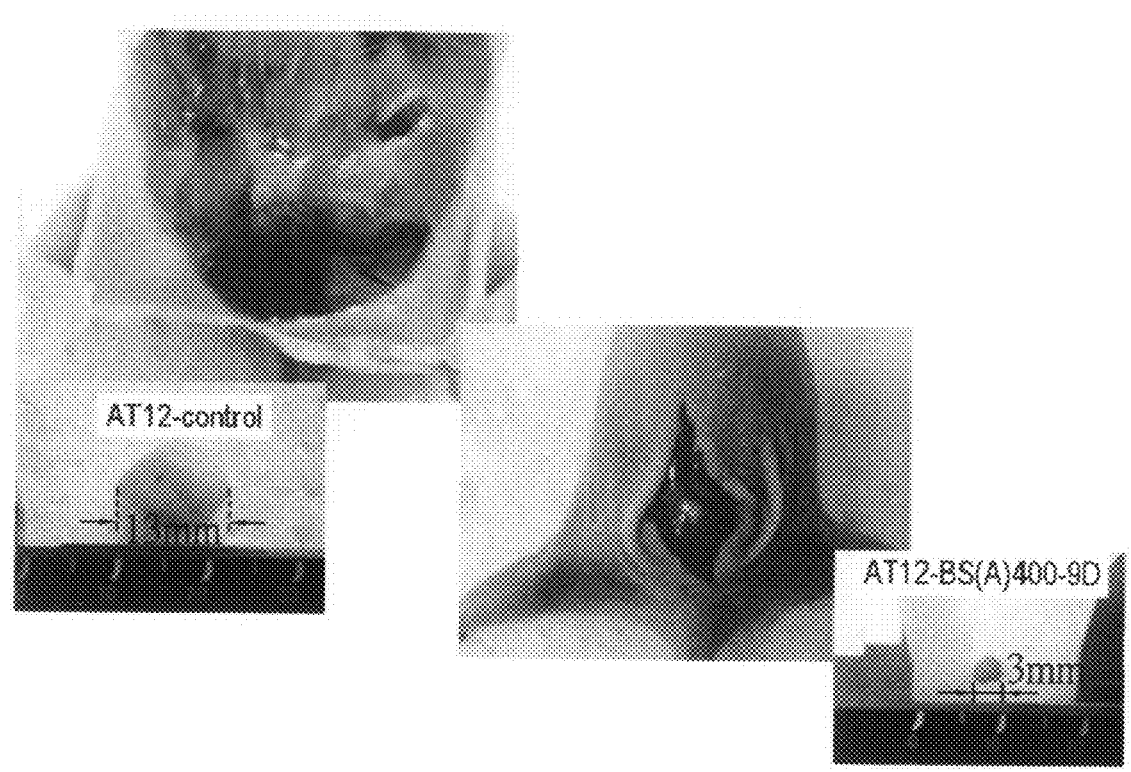
FIG. 13A are partial magnified pictures showing diameters of subcutaneous tumors taken one week after from a nude mouse inoculated with A549 tumor cells and I.P. administered with 500 mg/kg of BS-AE for 5 consecutive days.
Figure 13B:
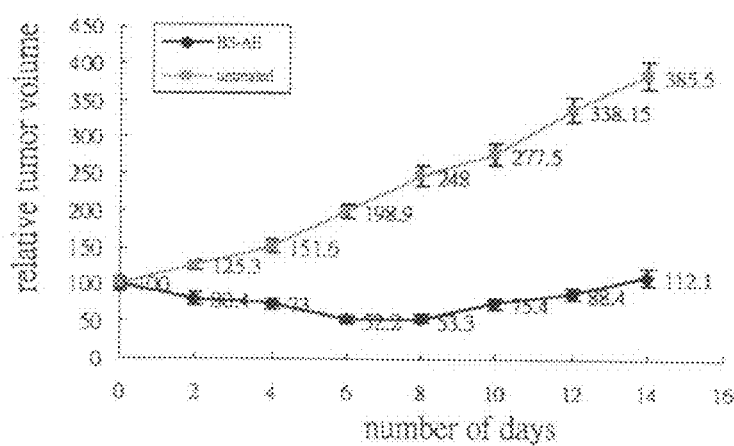
FIG. 13B is a curve showing relative volume changes of subcutaneous tumors from the mouse untreated and the mouse that is I.P. administered with 500 mg/kg of BS-AE with respect to the number of days for treatment.
Figure 14A:
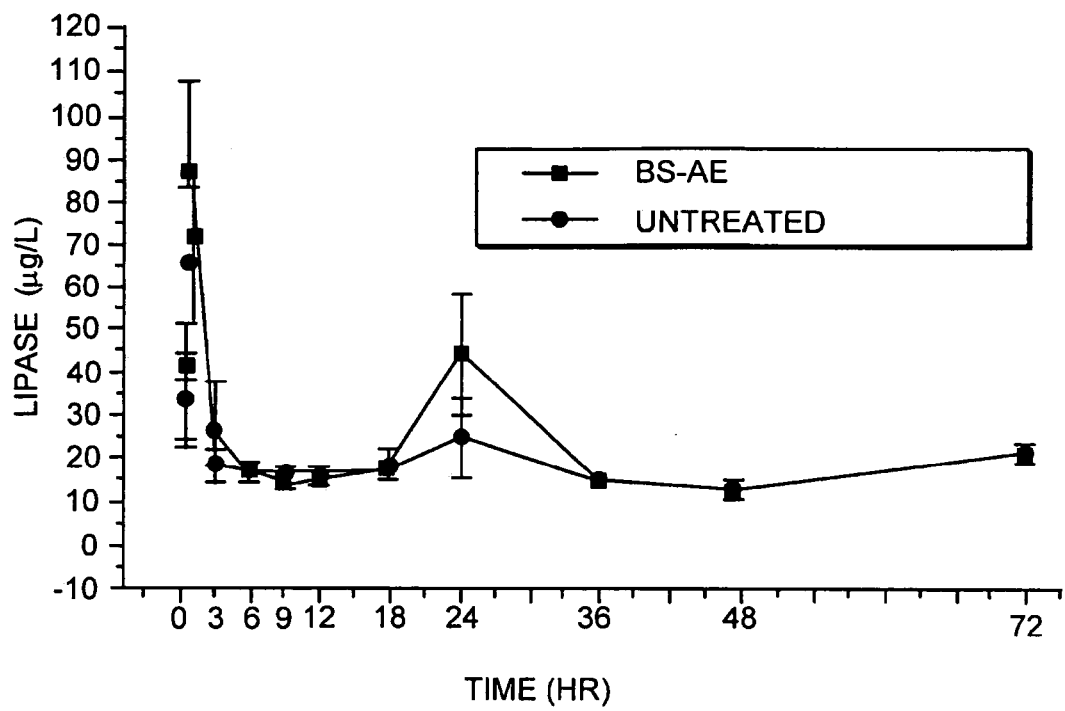
FIG. 14A through to 14H include a variety of statistical curves showing changes in indicative enzyme levels corresponding to the functionality of pancreas, liver, heart, kidney and hematopoietic systems in a conscious mouse within 72 hours after intravenous administration of 400 mg/kg of BS-AE to the mouse.
Figure 14B:
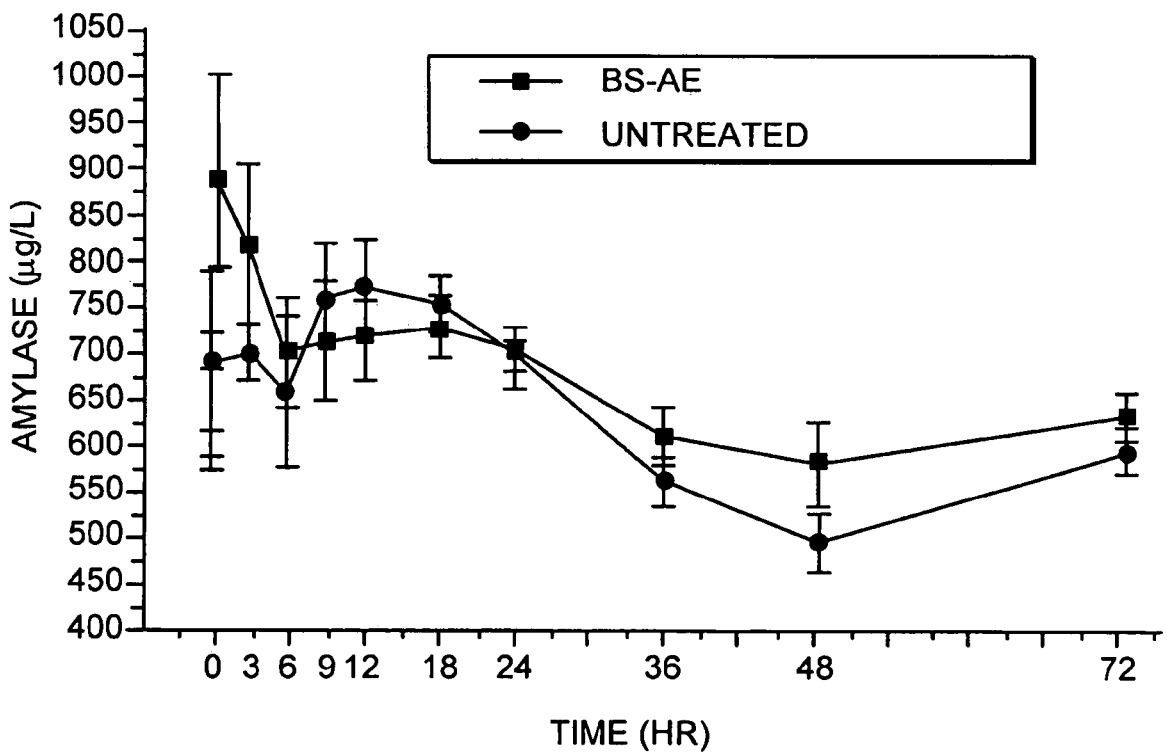
Figure 14C:
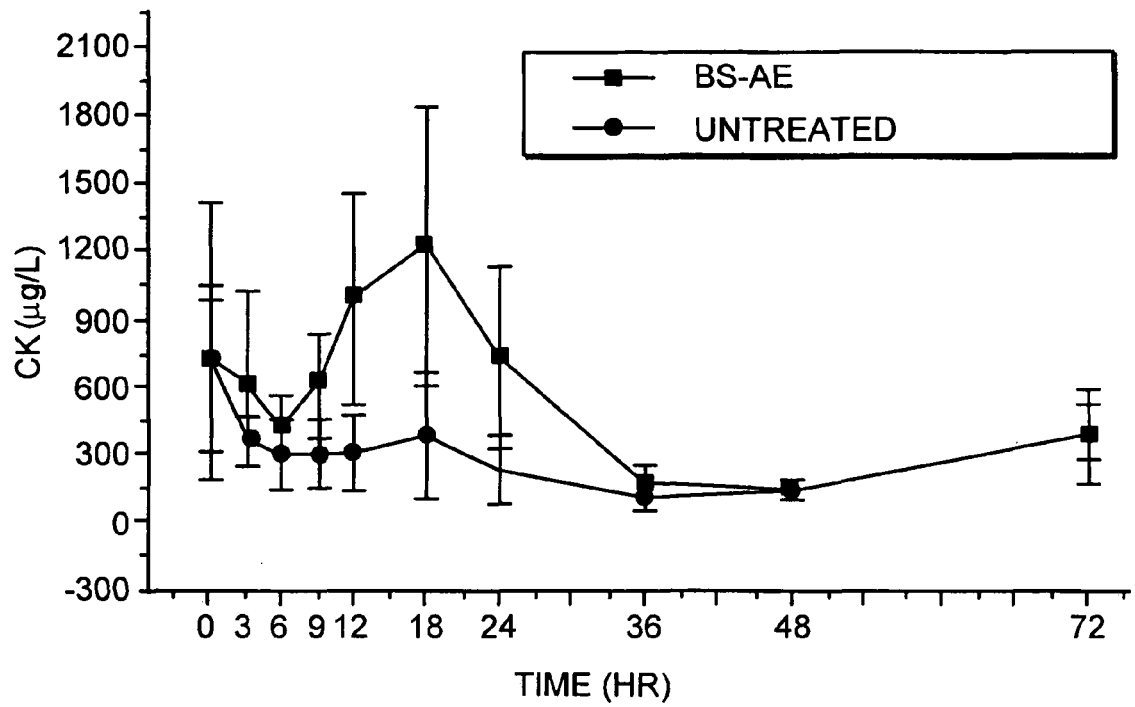
Figure 14D:
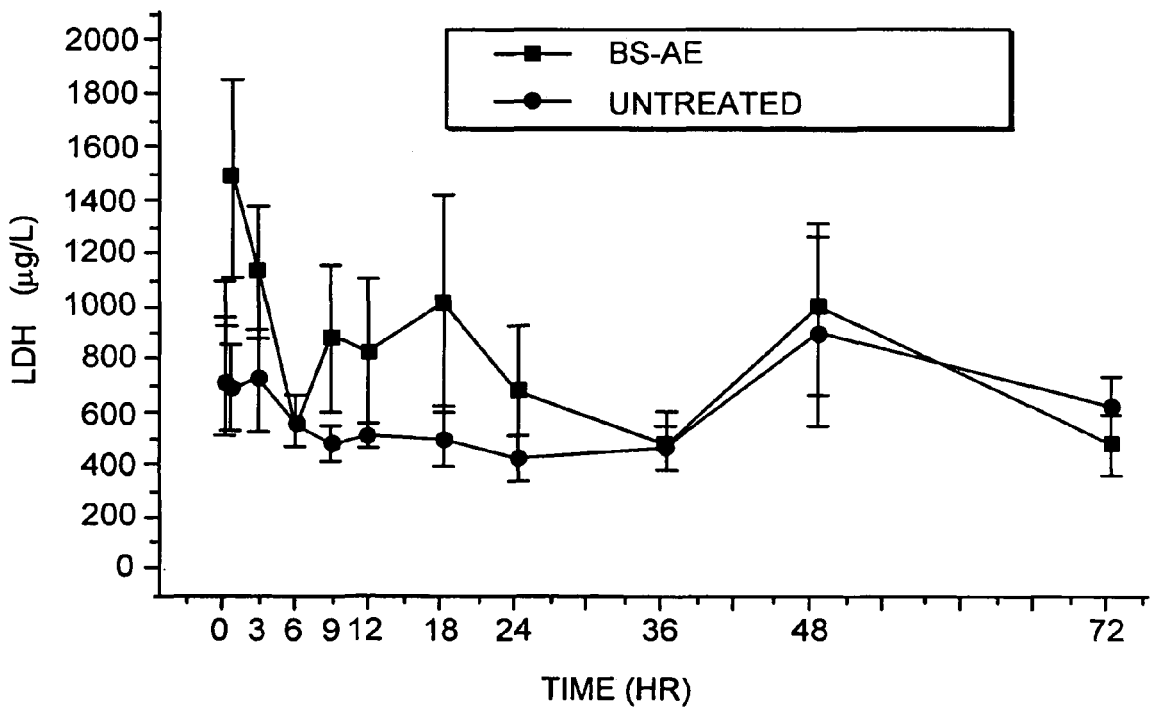
Figure 14E:
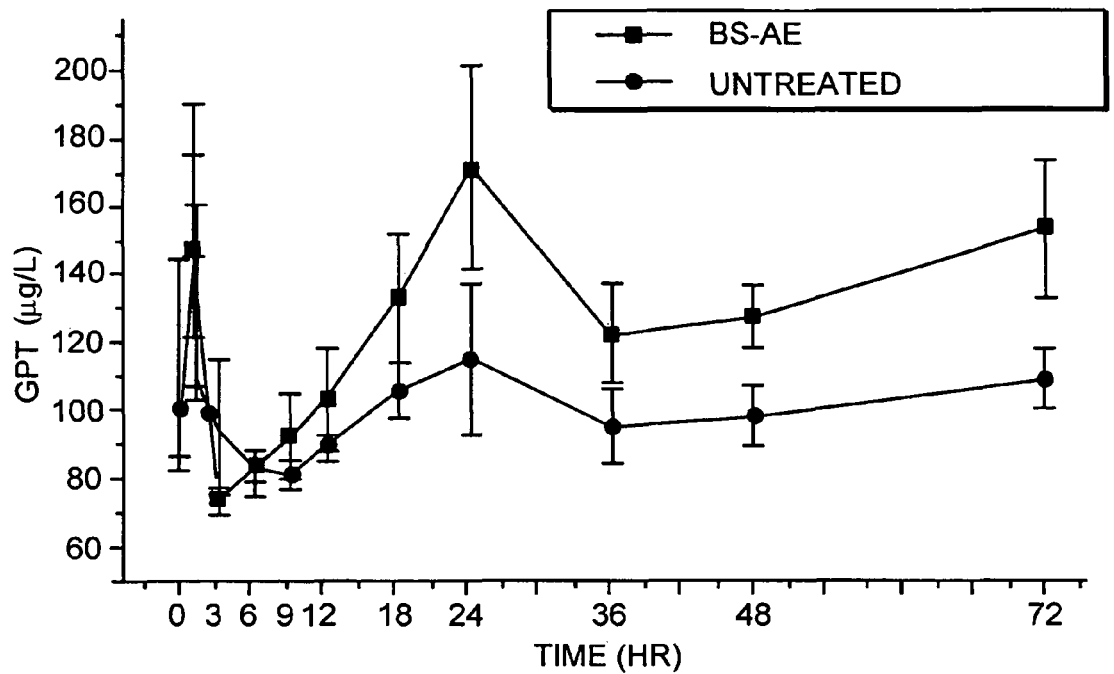
Figure 14F:
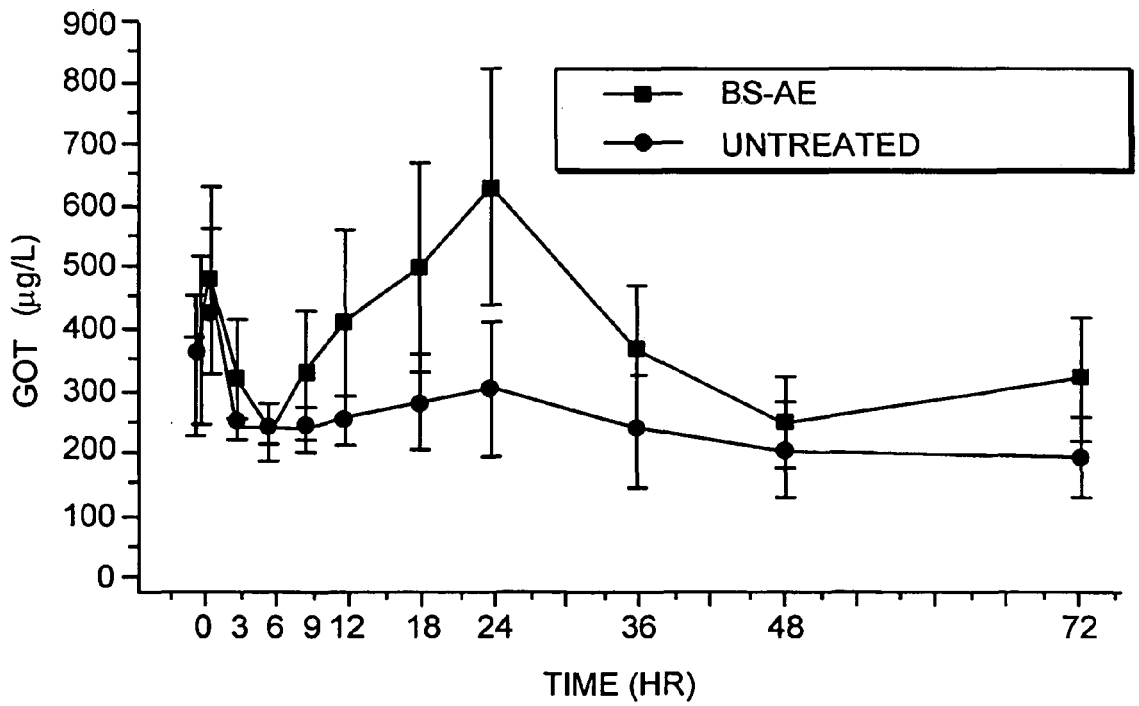
Figure 14G:
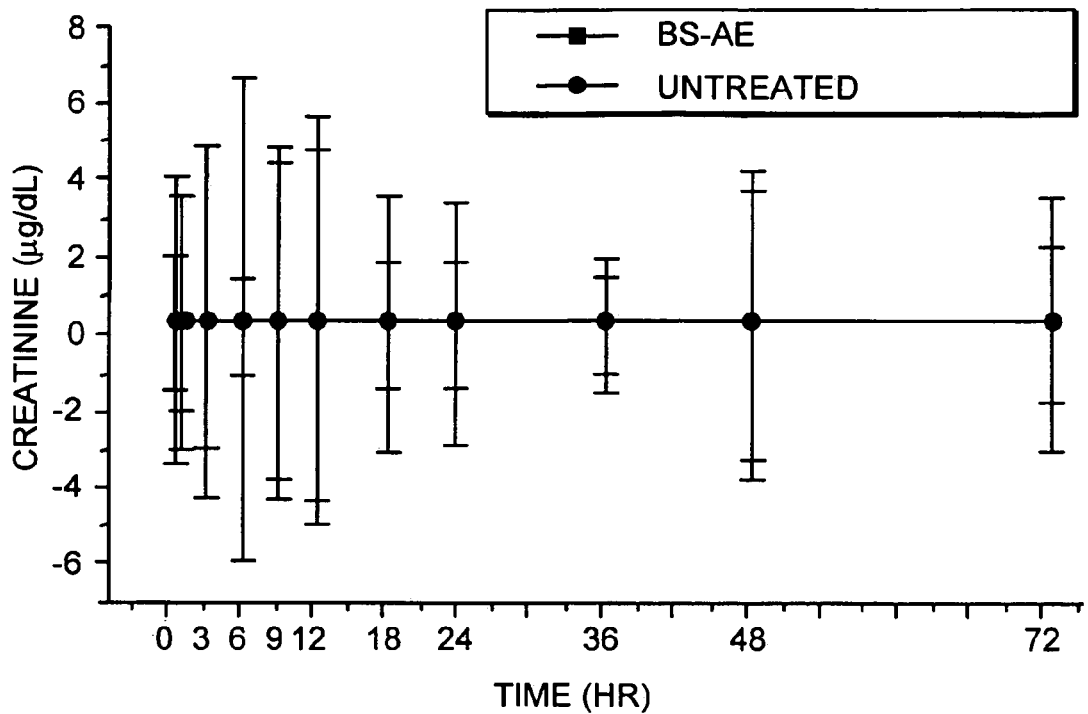
Figure 14H:
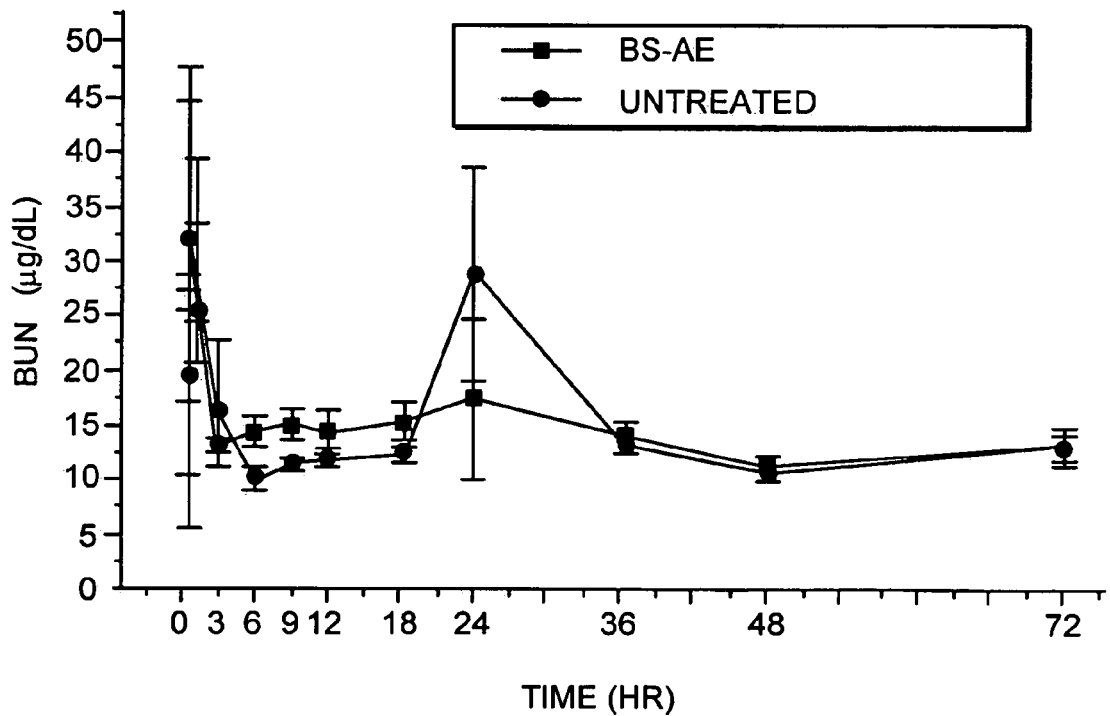
Figures 16A, 16B:
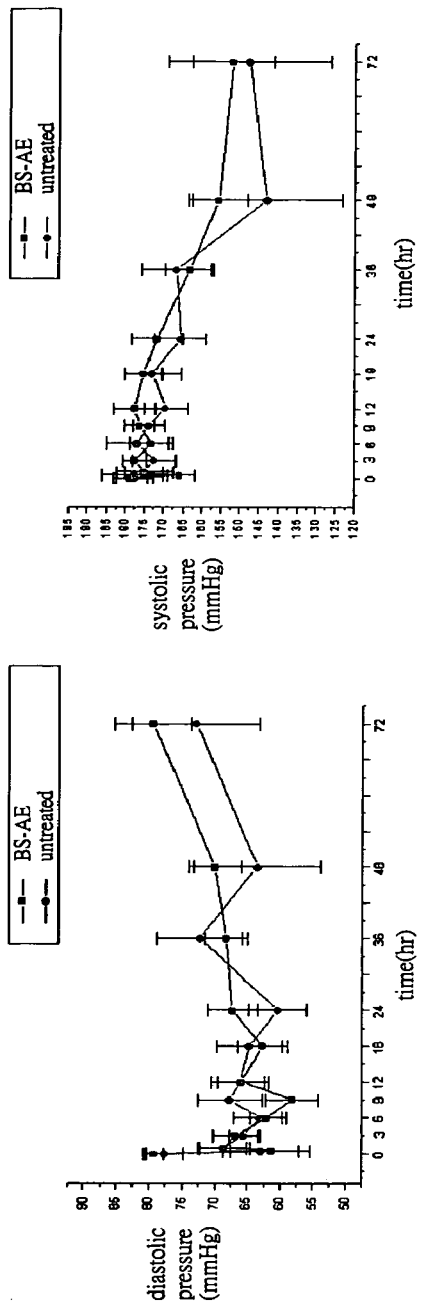
FIG. 16A through 16D include a variety of statistical curves showing changes in cardiac pulse, diastolic pressure, systolic pressure, and average blood pressure in the conscious mouse within 72 hours after intravenous administration of 400 mg/kg of BS-AE to the mouse.
Figures 16C, 16D:
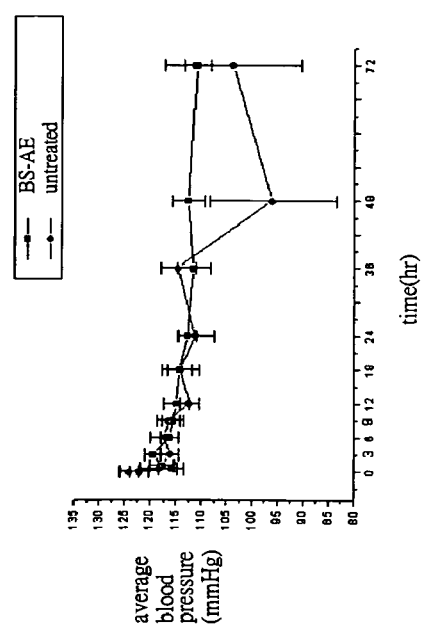
Figure 17:
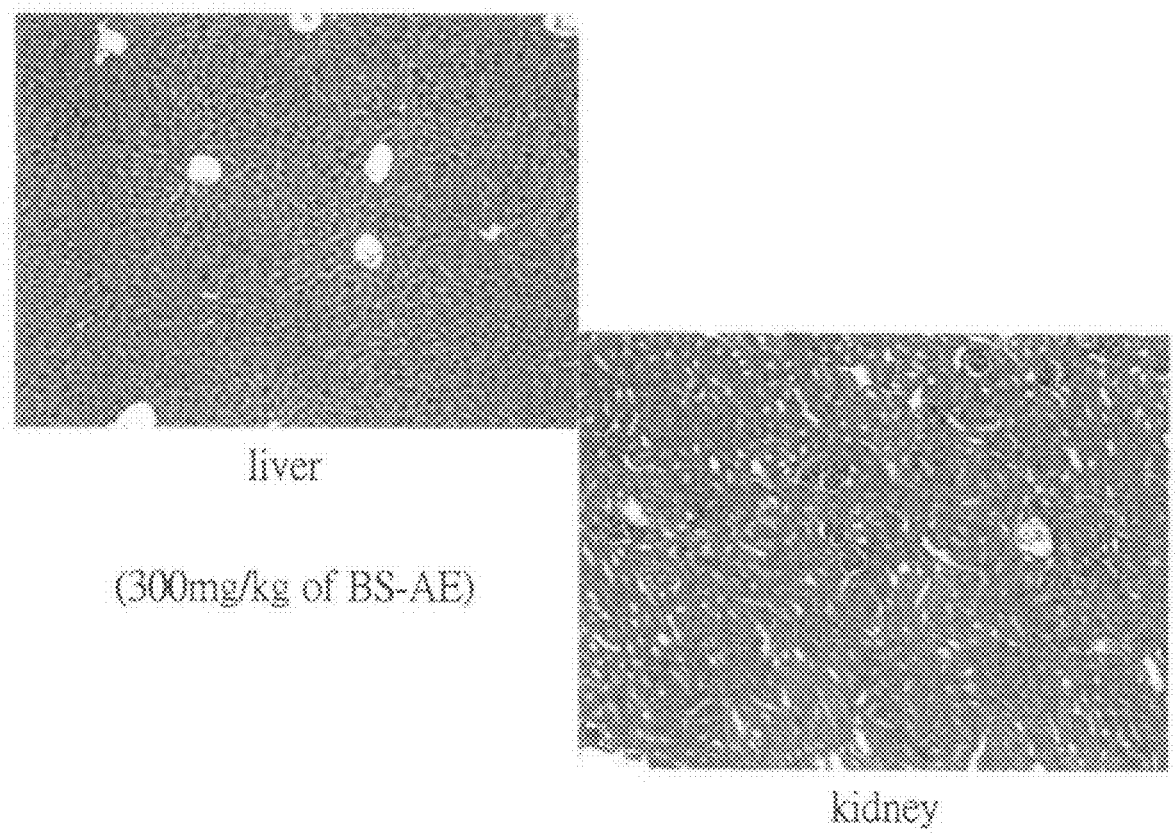
FIG. 17 includes histological sections illustrating liver cells and kidney cells of the conscious mouse after 300 mg/kg of BS-AE is I.P. administered to the mouse for 5 consecutive days.

The Estimate of the Tumor Inhibitory Effect of the γ-butyrolactone Compound and Pharmaceutical Composition thereof In Vivo Histological sections were examined to determine the tumor inhibitory effects of the γ-butyrolactone compound and pharmaceutical composition thereof on A549 cell and A549-T12 cells in vivo. FIGS. 11A, 11B, 12A, and 12B show the comparison of tumor tissue necrosis before and after the administration of BS-AE from 100× histological slide stained with haematoxylin and eosin stain (H&E stain). It is found that, infiltration of lymphocytes, a large extent of tumor cell hemorrhage, and tumor cell necrosis occur as 300 mg/kg or more of BS-AE is IP administered to animals for 5 days. FIG. 12B shows that after BS-AE treatment, only a few tumor cells remain from densely distributed tumor cells. As shown in the comparison FIG. 13A, the volume of tumor from subcutaneous tumor tissue (A549 cell line) clearly decrease by 77% (tumor diameter is reduced from 13 μm to 3 μm) after 500 mg/kg of BS-AE is given. From the tumor volume shown in FIG. 13B, it was found that the rate of tumor growth was clearly decreased after the tumor was treated with the *Bupleurum scorzonerifolium* extracts. Therefore, it can be understood from histological sections and hypodermic tumor tissue that the γ-butyrolactone compound and pharmaceutical composition thereof are cytotoxic in vivo and are effective in controlling the spreading rate of tumor volume.

Seventh Embodiment

The Cytotoxicity of *Bupleurum scorzonerifolium* Extracts on Cells and Animal Models It is known from the experimental result of this invention, BS-AE containing the γ-butyrolactone compound and pharmaceutical composition thereof have significant growth inhibitory effect on human hepatoma, lung cancer, ovarian cancer, breast cancer, malignant glioblastoma and colorectal carcinoma cells. As shown in Table 1, BS-AE and BS-8 (isochaiulactone) have cytotoxicity on A549 (lung cancer cell line), A549-T12 (taxol resistant A549 cubline), HT29 (colon cancer cell line), OVCAR-3 (ovarian cancen cell line), J5 (hepatocellular carcinoma), Hep G2 (Hepatocellular carcinoma), MCF 7 (breast cancer cell line), DBTRG-05MG (brian concern cell line (glioblastoma multiforme)) and WI-38 (embryonic fibroblast cell line). The acetone fraction of *Bupleurum scorzonerifolium* possesses strong cytotoxicity toward a wide variety of cancer cell lines.

TABLE 1

Cytotoxicity of *Bupleurum scorzonerifolium* extracts
Table 1. Cytotoxicity of *Bupleurum scorzonerifolium* extracts
Cytotoxicity of *Bupleurum scorzonerifolium* extracts
Cell Lines IC 50 (mg/ml) 24 hr

| Extract | A549 | A549-T12 | HT 29 | OVCAR-3 | J 5 | HepG2 | MCF 7 | DBTRG-05MG | WI 38 |
|---|---|---|---|---|---|---|---|---|---|
| Cisplatin | 17.2 ± 2.7 | — | — | — | — | — | — | — | 21.3 ± 4.5 |
| Taxol(nM) | 4 ± 0.6 | 20 ± 2.7 | 3 ± 0.5 | — | — | — | — | — | — |
| BS-AE | 58 ± 4 | 36 ± 2.5 | 55 ± 4.1 | 55 ± 5.5 | 48 ± 4 | 55 ± 4.5 | 60 ± 5 | 55 ± 4.5 | 150 ± 16 |
| BS-ME | 580 ± 36 | — | — | — | — | — | — | — | 510 ± 30 |
| BS-WE | >1,000[a] | — | — | — | — | — | — | — | >1,000[a] |
| BS-8 | 8 ± 0.8 | 1.7 ± 0.3 | 5 ± 0.8 | 7.2 ± 1.2 | 3.5 ± 0.7 | 5.5 ± 0.5 | 8 ± 0.8 | 7.5 ± 1 | — |

[a]Maximal dosage in this assay
BS-AE: *Bupleurum scorzonerifolium*-acetone crude extract
BS-ME: *Bupleurum scorzonerifolium*-methanol crude extract
BS-WE: *Bupleurum scorzonerifolium*-water crude extract
BS-8: isochalihulactone And from histological section and hypodermic tumor tissue examination, the γ-butyrolactone compound and pharmaceutical composition thereof were also cytotoxic to tumor tissue in vivo. Therefore, in order to further evaluate any possible harmful side effects on other normal cells and organs while the γ-butyrolactone compound and pharmaceutical composition thereof are cytotoxic to the tumors, a conscious rat administered with 400 μg/kg of BS-AE was used to show the change of all biochemical enzymes in the rat organs.

As shown in FIG. 14 and FIG. 15, after the conscious rat was administered with 400 µg/kg of BS-AE intravenously for 72 hours, there are no difference in the levels of Lipase, Amylase, glutamic oxaloacetic transaminase (GOT), glutamic pyruvic transaminase (GPT), Lactate Dehydrogenase (LDH), Creatinine Kinase (CK), Creatinine, Blood Urea Nitrogen (BUN), pulse, diastolic pressure, systolic pressure, platelets and white blood cells as compare to those of the control group without treatment. This indicates the intravenous (I.V.) administration of *Bupleurum scorzonerifolium* has no significant toxic effects for digestive, circulation, metabolic systems, haemopoietic mechanism and germ cells. The histological sections of the liver and kidney shown in FIG. 15 prove that the normal cells of liver and kidney are not destroyed after intraperitoneal (I.P.) administration of 300 µg/kg of BS-AE for 5 consecutive days. On the other hand, the γ-butyrolactone compound and pharmaceutical composition thereof have clearly inhibited the telomerase activity of the tumor cells in the living animal according to the above-mentioned results. Summarizing from all the results obtained previously, the γ-butyrolactone compound and pharmaceutical composition thereof administered in vivo has no effect on the normal cells or organ functions at the therapeutic dosage. Yet, the γ-butyrolactone compound and pharmaceutical composition thereof are cytotoxic with high specificity to the tumor cells including the Paclitaxel-resistant cell line. Thus, the γ-butyrolactone compound and pharmaceutical composition thereof may serve as a treatment drug or adjuvant to improve from current drug having incomplete cytotoxicity for the Paclitaxel-resistant tumor cells. Accordingly, the γ-butyrolactone compound and pharmaceutical composition thereof provide a new antineoplastic source to the cancer patients and those patients who developed resistance to Paclitaxel at the late stage of the chemotherapy.

Eighth Embodiment

The Synergistic Effect of *Bupleurum scorzonerifolium* Extracts on Other Anti-tumor Drugs According to the results from previous embodiment, it is understood that *Bupleurum scorzonerifolium* extracts, particularly BS-AE, isochaihulactone, and chaihulcatone are effective in inducing apoptosis to Paclitaxel-resistant cells, suggesting synergistic effect of the γ-butyrolactone compound and pharmaceutical composition thereof on Paclitaxel. In recent clinical treatment, two types of anti-tumor drugs, such as Cisplatin, Caroplatin, Bleomycin, Adriamycin, and Vinblastin are usually used in conjunction to improve survival rate of tumor patients at later stage and alleviate side effect of the drug. Therefore, the synergistic effect of the γ-butyrolactone compound and pharmaceutical composition thereof on the anti-tumor drug is estimated by comparing inhibitory effect on the growth of the tumor using either single anti-tumor drug or cocktail of the γ-butyrolactone compound and pharmaceutical composition thereof and the anti-tumor drugs.

Figure 18:
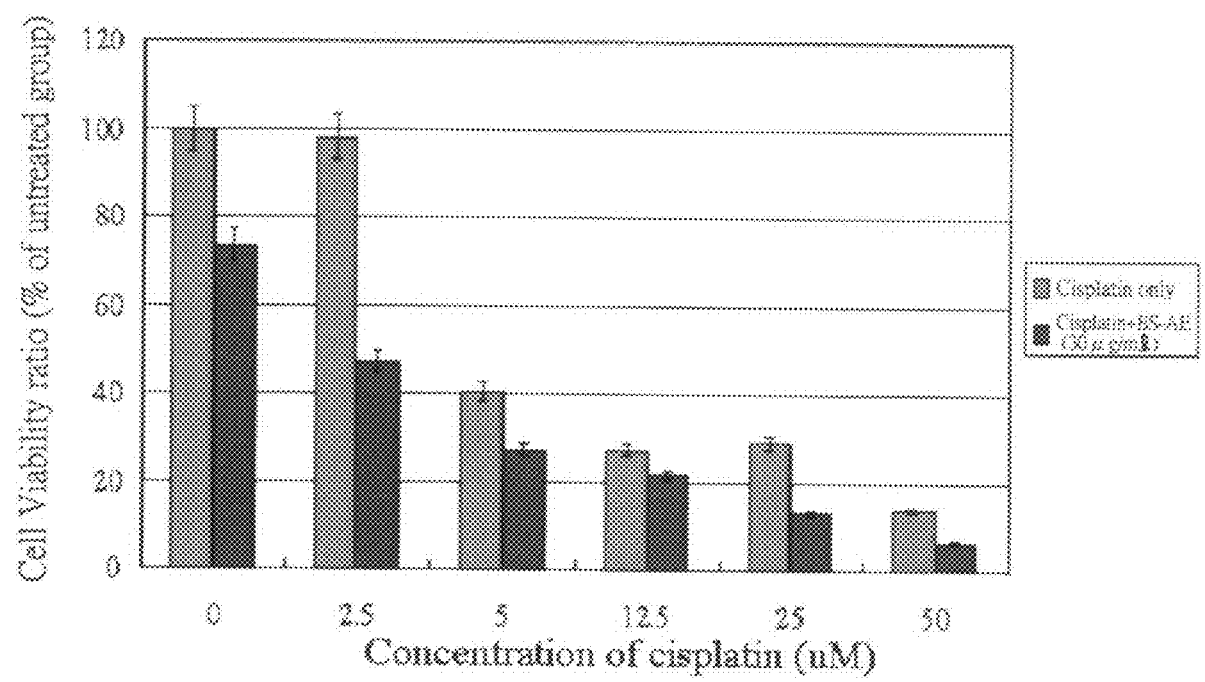
FIG. 18 is a bar chart showing cell viability ratio (in percentage of untreated group) for A549 cells either treated only with Cisplatin at different concentrations or treated with Cisplatin and 30 μg/ml of BS-AE.

The inhibitory effect on the growth of tumor cells is studied using A549 cells treated either with Cisplatin or Cisplatin and co-treatment of 30 µg/ml of BS-AE. As shown in FIG. 18, the cell viability ratio is significantly reduced when the cells were both treated with Cisplatin and BS-AE, as compared to the cell viability ratio when the cells were treated with Cisplatin alone. In other words, the same tumor growth inhibition can be achieved with less amount of anti-tumor drug administered when the anti-tumor drug is used in conjunction with BS-AE. Therefore, less cytotoxicity effect and side effect of the drug may be produced to affect the tumor patients receiving anti-tumor medication, while higher efficacy of anti-tumor treatment is achieved via synergistic effect of BS-AE on the anti-tumor drug.

Ninth Embodiment

Down-regulatory Effect of *Bupleurum scorzonerifolium* Extracts on Telomerase Activity The tumor inhibition effect in vivo is further measured to estimate the possibility of the γ-butyrolactone compound and pharmaceutical composition thereof as a new source of drug developement. A telomerase repeat amplification protocol (TRAP) assay utilizing radioactive γ-$^{32}$p-ATP is conducted to test telomerase activity of tumor after the γ-butyrolactone compound and pharmaceutical composition thereof are administered in the living animal inoculated with tumor cells, so as to determine whether BS-AE and isochaihulactone have a high specific cytotoxicity for the tumor cells.

Figure 19:
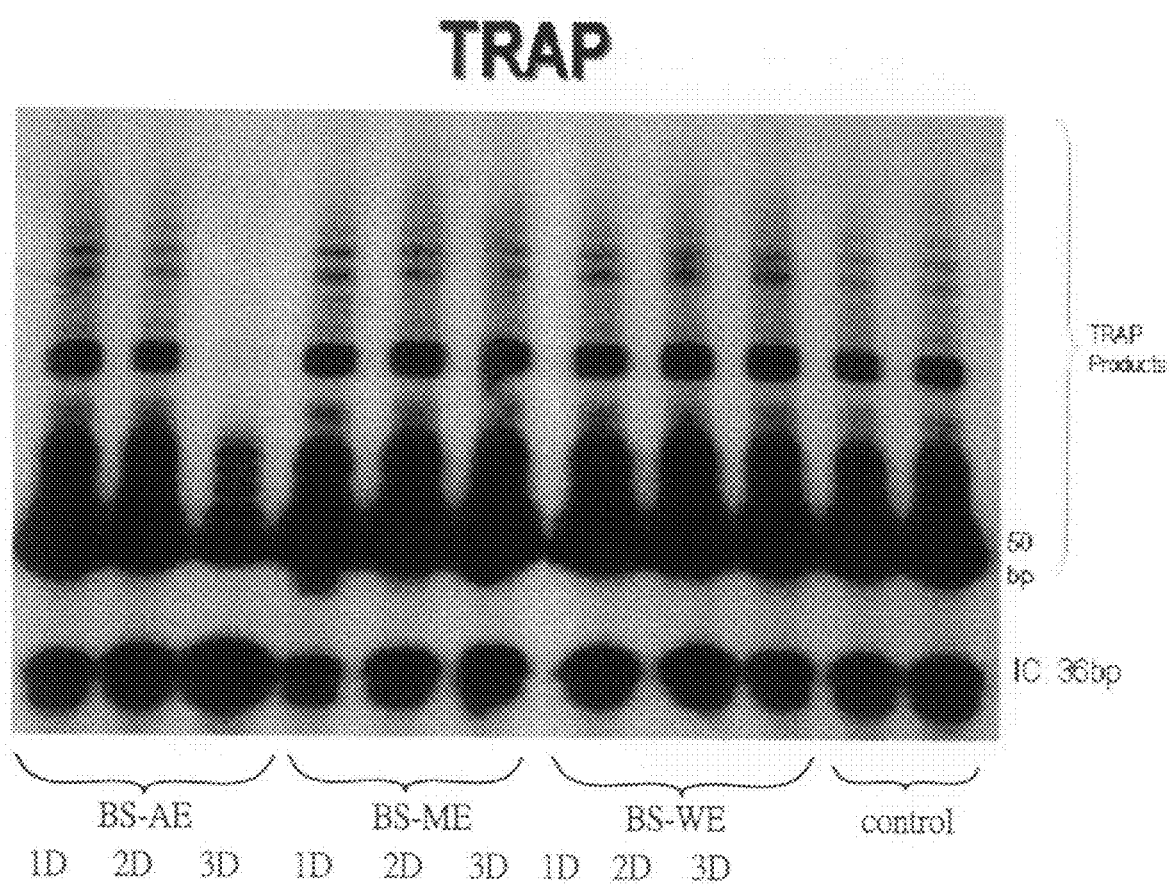
FIG. 19 is a TRAP assay analysis result showing telomerase activity of the A549 cells either treated with AZT (control), BS-AE, BS-ME, or BS-WE for 1 day (1D), 2 days (2D), and 3 days (3D)
Figure 20:
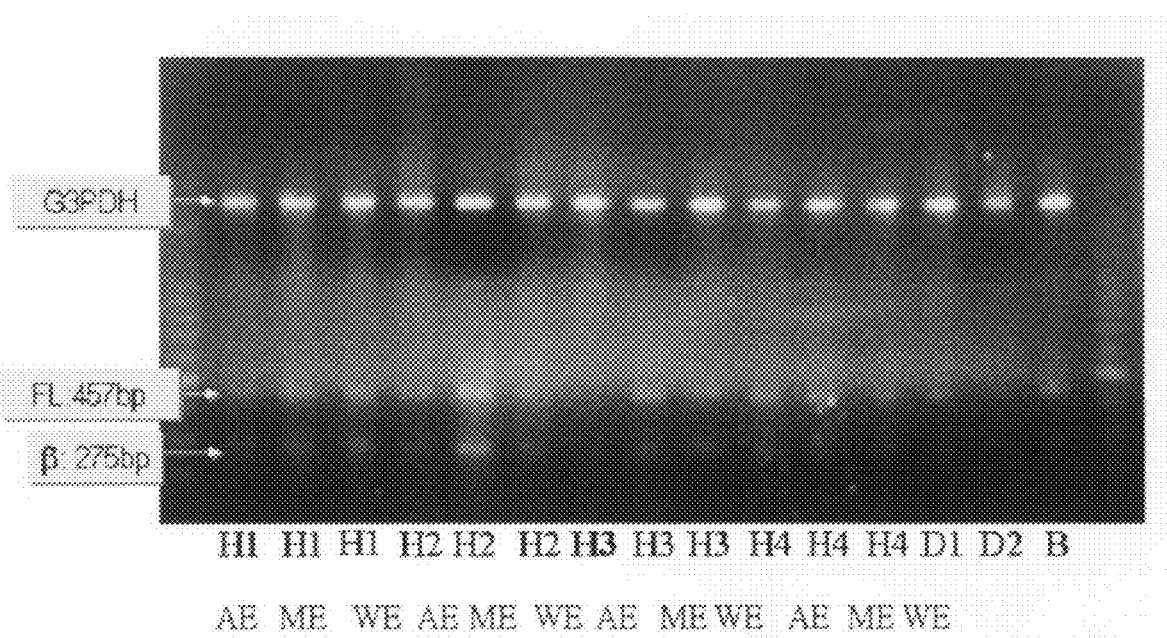
FIG. 20 is a blotting result of RT-PCR for mRNA expression of hTERT in the A549 cells treated with acetone extract (AE), methanol extract (ME), and water extract (WE) from selected Chinese herbs H1, H2, H3, and H4 (wherein H3 represents *Bupleurum scorzonerifolium*), and in the cells which are either untreated (B), or treated with DMSO at low (D1) and high (D2) concentrations (where FL represents hTERT in full length and β as a spliced variant form of hTERT subunit).

Referring to FIG. 19, the telomerase activity of the tumor cell was significantly reduced when the tumor cells A549 were treated with BS-AE. As it is evident from the current research that telomerase activity is regulated by hTERT, an anti-HIV agent, AZT that acts to down regulate expression of the hTERT gene is administered to the tumor cells A549. The down-regulatory effect of AZT is then compared with the γ-butyrolactone compound and pharmaceutical composition thereof. From FIG. 19, it is found the γ-butyrolactone compound and pharmaceutical composition thereof display a better inhibitory effect on the telomerase activity of the tumor cells than AZT, suggesting that the γ-butyrolactone compound and pharmaceutical composition thereof produce a stronger down-regulatory effect on expression of the hTERT gene than AZT. The down regulatory effect of the γ-butyrolactone compound and pharmaceutical composition thereof was further confirmed by results shown in FIG. 20, where extracts from several different Chinese herbs, such as were also included to compare with the γ-butyrolactone compound and pharmaceutical composition thereof for their roles in regulating expression of hTERT gene. As evident in FIG. 20, the expression of full length or spliced variant β of hTERT is suppressed following treatment with BS-AE, while the tumor cells treated with other extracts are not inhibited in expressing hTERT. Thus, it is very likely that the γ-butyrolactone compound and pharmaceutical composition thereof further provides anti-HIV effect other than AZT and other anti-HIV agents that act to inhibit telomerase activity. Also, the down regulation of telomerase activity of the γ-butyrolactone compound and pharmaceutical composition thereof may be applied as a therapeutic applications for anti RNA virus.

Accordingly, the present invention provides a γ-butyrolactone compound and pharmaceutical composition thereof as illustrated in the formula (I) below and having a Z or E configuration for its carbon 2(5) location. The γ-butyrolactone compound and pharmaceutical composition thereof include "isochaihulactone", "chaihulactone" and their derivatives which serve as active components for inhibiting tumor growth for hepatoma, ovarian cancer, lung cancer, malignant glioblastma or colorectal carcinoma.

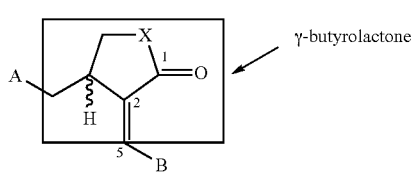

Formulae (I)

γ-butyrolactone wherein X=N, O, S, Se, and A, B can be selected from the following substituents:

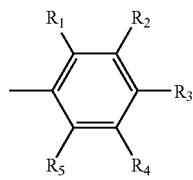

wherein R1, R2, R3, R4, R5 can be selected from a hydrogen atom, a halogen atom, a hydroxyl group, a mercapto group, an amino group, an alkoxy group, and a nitro group.

In accordance with the foregoing preferred embodiments of the invention, it is realised that the acetone crude extract being extracted from *Bupleurum scorzonerifolium* has more significant antineoplatic effects. Moreover, after applying BS-AE and isochaihulactone to both tumour cells and Paclitaxel-resistant tumour cells, they all show significant inhibition effects. And BS-AE could reduce telomerase activity, suppress cell proliferation, enhance cell apoptosis, and have in vivo anti tumour effect, while there is no significant toxicity to body systems such as digestive, circulation, metabolic systems, haemopoietic mechanism and genital system.

In terms of cell control mechanism, the γ-butyrolactone compound and pharmaceutical composition thereof act as a microtubule stabilizing agent, which promotes polymerization of β-tubulin inhibiting cancer cell mitosis and leading to cell death. The mechanism leading to cell death is similar to that of Paclitaxel for keeping the tumour cells arrested at G2/M stage of the cell cycle and inhibiting further cell proliferation.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A pharmaceutical composition for treating cell proliferative disorder, wherein the cell proliferative disorder is selected from hepatoma, ovarian cancer, breast cancer, human malignant glioblastoma, and human colorectal cancer, and develops drug-resistance when treated with Paclitaxel, comprising:

Cisplatin; and
a γ-butyrolactone compound shown in Formula (I) as an active ingredient:

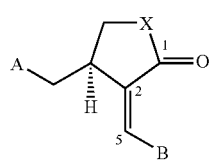

Formula (I)

wherein X=O; and A and B are each respectively

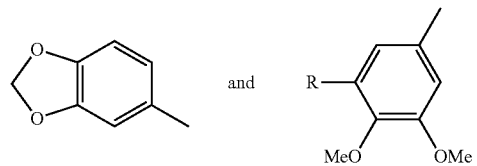

wherein R represents hydrogen atom or an alkoxy group.

2. The pharmaceutical composition of claim 1, wherein a carbon 2(5) position of the γ-butyrolactone compound is a heterocyclic compound having a Z configuration.

3. The pharmaceutical composition of claim 1, wherein a carbon 2(5) position of the γ-butyrolactone compound is a heterocyclic compound having an E configuration.

4. The pharmaceutical composition of claim 1, wherein the γ-butyrolactone compound is shown in Formula (II) and is named Chaihulactone:

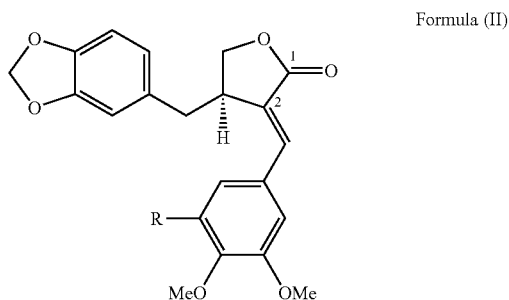

Formula (II)

wherein R represents an alkoxy group.

5. The pharmaceutical composition of claim 1, wherein the γ-butyrolactone compound is shown in Formula (III) and is named Isochaihulactone

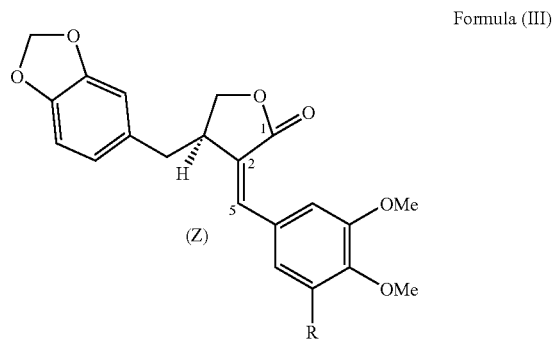

Formula (III)

wherein R represents hydrogen atom, or alkoxy group.

* * * * *